United States Patent
Naito et al.

(10) Patent No.: US 12,319,587 B2
(45) Date of Patent: Jun. 3, 2025

(54) COMPOUND, COMPOSITION, FILM, LAYERED STRUCTURE, LIGHT-EMITTING DEVICE, AND DISPLAY

(71) Applicant: Sumitomo Chemical Company, Limited, Tokyo (JP)

(72) Inventors: Shota Naito, Tsukuba (JP); Mizuho Sugiuchi, Tsukuba (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 781 days.

(21) Appl. No.: 17/435,112

(22) PCT Filed: Feb. 21, 2020

(86) PCT No.: PCT/JP2020/006988
§ 371 (c)(1),
(2) Date: Aug. 31, 2021

(87) PCT Pub. No.: WO2020/179489
PCT Pub. Date: Sep. 10, 2020

(65) Prior Publication Data
US 2022/0135421 A1 May 5, 2022

(30) Foreign Application Priority Data
Mar. 1, 2019 (JP) .................. 2019-037918

(51) Int. Cl.
| | |
|---|---|
| *C01G 21/00* | (2006.01) |
| *C09K 11/02* | (2006.01) |
| *C09K 11/66* | (2006.01) |
| *H10H 20/851* | (2025.01) |
| *H10K 85/50* | (2023.01) |

(52) U.S. Cl.
CPC ............ *C01G 21/006* (2013.01); *C09K 11/02* (2013.01); *C09K 11/025* (2013.01); *C09K 11/664* (2013.01); *H10H 20/8512* (2025.01); *H10K 85/50* (2023.02); *C01P 2002/34* (2013.01); *C01P 2004/62* (2013.01); *C01P 2004/64* (2013.01); *C01P 2006/60* (2013.01)

(58) Field of Classification Search
CPC ..... C09K 11/664; C09K 11/02; C09K 11/025; C01G 21/006; H01L 33/502; H10K 85/50; C01P 2002/34; C01P 2004/64
See application file for complete search history.

(56) References Cited

U.S. PATENT DOCUMENTS

| | | | |
|---|---|---|---|
| 2017/0084848 A1* | 3/2017 | Gao | ............ C09K 11/664 |
| 2020/0168666 A1* | 5/2020 | Naito | ............ C09K 11/665 |

FOREIGN PATENT DOCUMENTS

| | | | | |
|---|---|---|---|---|
| TW | 201900757 A | | 1/2019 | |
| WO | WO-2018212260 A1 * | | 11/2018 | ............ B32B 27/20 |
| WO | WO 2019/100041 | * | 5/2019 | |

OTHER PUBLICATIONS

Ding el al. Flexible Piezoelectric Nanocomposite Generators Based on Formamidinium Lead Halide Perovskite nanopartides. Advanced Functional Materials, 26 1-9 (2016).*
Hanusch et al.. Efficient Planar Heterojunction Perovskite Solar Cells Based on Formamidinium Lead Bromide, J. Phys. Chem. Lett., 2014,5,2791-2795.*
Notice of Reasons for Refusal issued in Japanese Patent Application No. 2019-037918 drafted Nov. 22, 2022.
Notice of Submission of Publication filed in Japanese Patent Application No. 2019-037918 dated Feb. 25, 2022.
Third Party Observations filed in Japanese Patent Application No. 2019-37918 dated Feb. 7, 2022.
Notice of Submission of Publication issued in Japanese Patent Application No. 2019-037918 dated Mar. 31, 2023.
Third Party Observations filed in Japanese Patent Application No. 2019-037918 dated Mar. 15, 2023.
Notification of Submission of Publications issued in Japanese Patent Application No. 2019-037918 dated Mar. 31, 2023.
Notice of Reasons for Refusal issued in Japanese Patent Application No. 2019-037918 drafted Apr. 11, 2023.
Third Party Observation filed in International Patent Application No. PCT/JP2020/006988 dated Mar. 15, 2021.
Liu et al., "Toward Highly Luminescent and Stabilized Silica-Coated Perovskite Quantum Dots through Simply Mixing and Stirring under Room Temperature in Air," ACS Applied Materials & Interfaces, 10: 13053-13061 (2018).
Yang et al., "In situ silica coating-directed synthesis of orthorhombic methylammonium lead bromide perovskite quantum dots with high stability," Journal of Colloid and Interface Science, 509: 32-38 (2018).
Office Action issued in Japanese Patent Application No. 2020-139119 drafted Aug. 29, 2023.
Ding et al. Flexible Piezoelectric Nanocomposite Generators Based on Formamidinium Lead Halide Perovskite Nanoparticles, Advanced Functional Materials, 26 1-9 (2016).

(Continued)

*Primary Examiner* — C Melissa Koslow
(74) *Attorney, Agent, or Firm* — Morgan, Lewis & Bockius LLP

(57) ABSTRACT

A compound has a perovskite type crystal structure containing A which is a monovalent cation, B which is a metal ion, and X which is a halide ion as components. The perovskite type crystal structure has a unit cell volume of 0.2000 nm$^3$ or more and 0.2150 nm$^3$ or less, an ionic radius of B of 0.7 Å or more and 1.4 Å or less, and an ionic radius of X of 0.5 Å or more and 2.5 Å or less.

17 Claims, 1 Drawing Sheet

(56) References Cited

OTHER PUBLICATIONS

First Office Action issued in corresponding Taiwanese Patent Application No. 2020-43434 dated Aug. 4, 2023.
International Search Report issued in corresponding International Patent Application No. PCT/JP2020/006988 dated Apr. 7, 2020.
Office Action dated Feb. 19, 2024, issued in corresponding Taiwanese Patent Application No. 109106230.
Shannon, R. D., Revised Effective Ionic Radii and Systematic Studies of Interatomic Distances in Halides and Chalcogenides. Acta Crystallographica, 751-767, A32 (1976).†
Lattice Constant, Retrieved Nov. 4, 2022 from https://en.wikipedia.org/wiki/Lattice_constant.†

\* cited by examiner
† cited by third party

COMPOUND, COMPOSITION, FILM, LAYERED STRUCTURE, LIGHT-EMITTING DEVICE, AND DISPLAY

TECHNICAL FIELD

The present invention relates to a compound, a composition, a film, a layered structure, a light-emitting device, and a display.

BACKGROUND ART

In recent years, there has been increasing interest in a compound having a perovskite type crystal structure with a high quantum yield as a light-emitting material. For example, Non-Patent Document 1 reports emission characteristics of a compound having a perovskite type crystal structure.

PRIOR ART DOCUMENTS

Non-Patent Document

Non-Patent Document 1: Organic Electronics 60 (2018) 64-70

SUMMARY OF THE INVENTION

Problems to be Solved by the Invention

However, the quantum yield of the compound having a perovskite type crystal structure described in Non-Patent Document 1 is insufficient for use in a light-emitting device, a display, or the like.

The present invention has been achieved in view of the above problem, and an object of the present invention is to provide a compound having a perovskite type crystal structure with a high quantum yield, a composition containing the compound, a film containing the composition, a layered structure including the film, and a light-emitting device and a display each including the layered structure.

Means for Solving the Problems

The present inventors made intensive studies in order to solve the above problem, and as a result, have reached the following invention.

The present invention includes the following [1] to [12].

[1] A compound having a perovskite type crystal structure containing A, B, and X as components, in which the perovskite type crystal structure has a unit cell volume of 0.2000 nm$^3$ or more and 0.2150 nm$^3$ or less, an ionic radius of B of 0.7 Å or more and 1.4 Å or less, and an ionic radius of X of 0.5 Å or more and 2.5 Å or less.

(A is a component located at each apex of a hexahedron centered on B in the perovskite type crystal structure, and is a monovalent cation.

X is a component located at each apex of an octahedron centered on B in the perovskite type crystal structure, and is a halide ion.

B is a component located at the center of the hexahedron with A at an apex and the octahedron with X at an apex in the perovskite type crystal structure, and is a metal ion.)

[2] The compound according to [1], in which the A is at least one cation selected from the group consisting of an organic ammonium ion and an amidinium ion.

[3] The compound according to [1] or [2], in which the B is at least one metal ion selected from the group consisting of a lead ion, a tin ion, an antimony ion, and a bismuth ion.

[4] The compound according to any one of [1] to [3], in which the X is a bromide ion.

[5] A composition containing the compound according to any one of [1] to [4] and at least one compound selected from the group consisting of the following (2-1), a modified product of the following (2-1), the following (2-2), and a modified product of the following (2-2).

(2-1) Silazane (2-2) Silicon compound having at least one group selected from the group consisting of an amino group, an alkoxy group, and an alkylthio group

[6] A composition containing the compound according to any one of [1] to [4], and at least one selected from the group consisting of the following (3), the following (4), and the following (5).

(3) Solvent (4) Polymerizable compound (5) Polymer

[7] The composition according to [5], further containing at least one selected from the group consisting of the following (3), the following (4), and the following (5).

(3) Solvent (4) Polymerizable compound (5) Polymer

[8] A film containing the compound according to any one of [1] to [4].

[9] A film containing the composition according to any one of [5] to [7].

[10] A layered structure including the film according to [8] or [9].

[11] A light-emitting device including the layered structure according to.

[12] A display including the layered structure according to [10].

Effect of the Invention

The present invention can provide a compound having a perovskite type crystal structure with a high quantum yield, a composition containing the compound, a film containing the composition, a layered structure including the film, and a light-emitting device and a display each including the layered structure.

MODE FOR CARRYING OUT THE INVENTION

Figure 1:
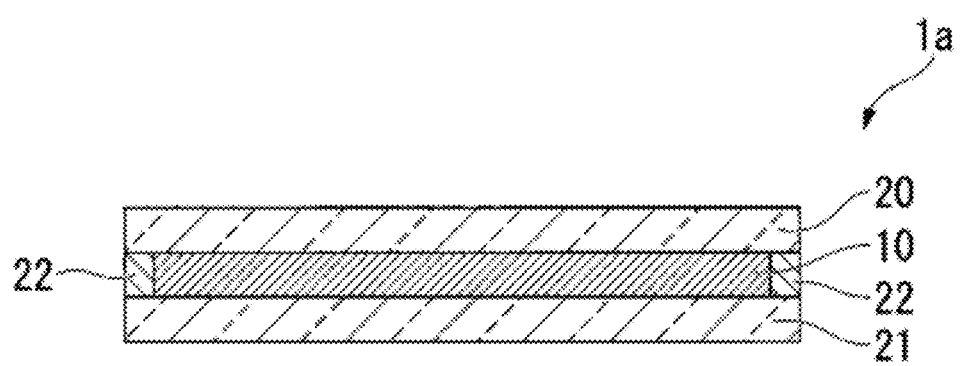
FIG. 1 is a cross-sectional view illustrating an embodiment of a layered structure according to the present invention.

Hereinafter, the present invention will be described in detail with reference to an embodiment.

<Compound Having Perovskite Type Crystal Structure>

A compound of the present embodiment is a compound having a perovskite type crystal structure having a unit cell volume of 0.2000 nm$^3$ or more and 0.2150 nm$^3$ or less and containing A, B, and X as components (hereinafter, also referred to as "(1) perovskite compound" or simply "(1)").

A is a component located at each apex of a hexahedron centered on B in the perovskite type crystal structure, and is a monovalent cation.

B is a component located at the center of the hexahedron with A at an apex and an octahedron with X at an apex in the perovskite type crystal structure, and is a metal ion having an ionic radius of 0.7 Å or more and 1.4 Å or less. B is preferably a metal cation capable of taking an octahedral coordination of X.

X is a component located at each apex of the octahedron centered on B in the perovskite type crystal structure, and is a halide ion having an ionic radius of 0.5 Å or more and 2.5 Å or less.

The structure of the perovskite compound containing A, B, and X as components may be any of a three-dimensional structure, a two-dimensional structure, and a quasi-two-dimensional structure.

In a case of the three-dimensional structure, the composition formula of the perovskite compound is represented by $ABX_{(3+\delta)}$.

In a case of the two-dimensional structure, the composition formula of the perovskite compound is represented by $A_2BX_{(4+\delta)}$.

Here, $\delta$ is a number that can be appropriately changed depending on a charge balance of B, and is −0.7 or more and 0.7 or less. For example, when A is a monovalent cation, B is a divalent cation, and X is a monovalent anion, $\delta$ can be selected such that the perovskite compound is electrically neutral. The state in which the perovskite compound is electrically neutral means that the charge of the perovskite compound is zero.

The perovskite compound contains an octahedron centered on B with X at an apex. The octahedron is represented by $BX_6$.

When the perovskite compound has a three-dimensional structure, the $BX_6$ contained in the perovskite compound shares one X located at an apex of the octahedron ($BX_6$) with two adjacent octahedrons ($BX_6$) in the crystal, and thereby constitutes a three-dimensional network.

When the perovskite compound has a two-dimensional structure, the $BX_6$ contained in the perovskite compound shares two Xs located at apexes of the octahedron ($BX_6$) with two adjacent octahedrons ($BX_6$) in the crystal, thereby shares a ridgeline of the octahedron, and constitutes a two-dimensionally connected layer. The perovskite compound has a structure in which a two-dimensionally connected layer formed of $BX_6$ and a layer formed of A are alternately stacked.

Here, the crystal structure of the perovskite compound can be confirmed with an X-ray diffraction pattern.

When the perovskite compound has a perovskite type crystal structure having a three-dimensional structure, a peak derived from (hkl)=(001) is usually confirmed at a position of 2θ=12 to 18° in an X-ray diffraction pattern. Alternatively, a peak derived from (hkl)=(110) is confirmed at a position of 2θ=18 to 25°.

When the perovskite compound has a perovskite type crystal structure having a three-dimensional structure, preferably, a peak derived from (hkl)=(001) is confirmed at a position of 2θ=13 to 16°, or a peak derived from (hkl)=(110) is confirmed at a position of 2θ=20 to 23°.

When the perovskite compound has a perovskite type crystal structure having a two-dimensional structure, a peak derived from (hkl)=(002) is usually confirmed at a position of 2θ=1 to 10° in an X-ray diffraction pattern. A peak derived from (hkl)=(002) is preferably confirmed at a position of 2θ=2 to 8°.

The perovskite compound preferably has a three-dimensional structure.

The unit cell volume of the perovskite compound is 0.2000 nm³ or more and 0.2150 nm³ or less. The unit cell volume is preferably 0.2060 nm³ or more and 0.2150 nm³ or less, more preferably 0.2077 nm³ or more and 0.2150 nm³ or less, still more preferably 0.2077 nm³ or more and 0.2135 nm³ or less, and most preferably 0.2080 nm³ or more and 0.2128 nm³ or less from a viewpoint of sufficiently improving emission characteristics. When the unit cell volume of the perovskite compound is within the above range, defects in the crystal structure in the perovskite compound are reduced, and the quantum yield is improved.

Here, the unit cell volume of (1) perovskite compound can be determined by calculating an interplanar spacing of a unit cell from an X-ray diffraction pattern obtained by X-ray diffraction measurement with a CuKα ray using Bragg's formula and determining a cube of the interplanar spacing of the unit cell. Specifically, the unit cell volume can be determined by the following formula 1.

$$\text{Unit cell volume (nm}^3\text{)}=(\lambda/(2\cdot\sin\theta))^3 \quad \text{Formula 1}$$

In the formula 1, λ is 0.15418 nm. As θ, a value of 2θ corresponding to a peak having the strongest intensity among peaks corresponding to (hkl)=(100) of (1) perovskite compound is adopted.

(Component A)

A constituting the perovskite compound is a monovalent cation. Examples of A include a cesium ion, an organic ammonium ion, and an amidinium ion, and an organic ammonium ion and an amidinium ion are preferable.

(Organic Ammonium Ion)

Specific examples of the organic ammonium ion serving as A include a cation represented by the following formula (A3).

[Chemical formula 1]

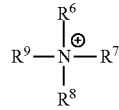

(A3)

In formula (A3), $R^6$ to $R^9$ each independently represent a hydrogen atom, an alkyl group, or a cycloalkyl group. However, at least one of $R^6$ to $R^9$ is an alkyl group or a cycloalkyl group, and not all of $R^6$ to $R^9$ are hydrogen atoms at the same time.

The alkyl groups represented by $R^6$ to $R^9$ may be linear or branched. The alkyl groups represented by $R^6$ to $R^9$ may each independently have an amino group as a substituent.

The alkyl groups represented by $R^6$ to $R^9$ each independently usually have 1 to 20 carbon atoms, preferably have 1 to 4 carbon atoms, more preferably have 1 to 3 carbon atoms, and still more preferably have 1 carbon atom.

The cycloalkyl groups represented by $R^6$ to $R^9$ may each independently have an amino group as a substituent.

The cycloalkyl groups represented by $R^6$ to $R^9$ each independently usually have 3 to 30 carbon atoms, preferably have 3 to 11 carbon atoms, and more preferably have 3 to 8 carbon atoms. The number of carbon atoms includes the number of carbon atoms of a substituent.

The groups represented by $R^6$ to $R^9$ are each independently preferably a hydrogen atom or an alkyl group.

When the perovskite compound contains the organic ammonium ion represented by the above formula (A3) as A, the number of alkyl groups and cycloalkyl groups that can be contained in formula (A3) is preferably small. In addition, the number of carbon atoms of the alkyl groups and the cycloalkyl groups that can be contained in formula (A3) is preferably small. As a result, a perovskite compound having a three-dimensional structure with high emission intensity can be obtained.

In the organic ammonium ion represented by formula (A3), the total number of carbon atoms contained in the alkyl groups and the cycloalkyl groups represented by $R^6$ to $R^9$ is preferably 1 to 4. In addition, in the organic ammonium ion represented by formula (A3), more preferably, one of $R^6$ to $R^9$ is an alkyl group having 1 to 3 carbon atoms, and three of $R^6$ to $R^9$ are hydrogen atoms.

Examples of the alkyl groups of $R^6$ to $R^9$ include a methyl group, an ethyl group, a n-propyl group, an isopropyl group, a n-butyl group, an isobutyl group, a sec-butyl group, a tert-butyl group, a n-pentyl group, an isopentyl group, a neopentyl group, a tert-pentyl group, a 1-methylbutyl group, a n-hexyl group, a 2-methylpentyl group, a 3-methylpentyl group, a 2,2-dimethylbutyl group, a 2,3-dimethylbutyl group, a n-heptyl group, a 2-methylhexyl group, a 3-methylhexyl group, a 2,2-dimethylpentyl group, a 2,3-dimethylpentyl group, a 2,4-dimethylpentyl group, a 3,3-dimethylpentyl group, a 3-ethylpentyl group, a 2,2,3-trimethylbutyl group, a n-octyl group, an isooctyl group, a 2-ethylhexyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, and an icosyl group.

Examples of the cycloalkyl groups of $R^6$ to $R^9$ include cycloalkyl groups in which the alkyl groups having 3 or more carbon atoms, which have been exemplified for the alkyl groups of $R^6$ to $R^9$, each independently form a ring. Examples thereof include a cyclopropyl group, a cyclobutyl group, a cyclopentyl group, a cyclohexyl group, a cycloheptyl group, a cyclooctyl group, a cyclononyl group, a cyclodecyl group, a norbornyl group, an isobornyl group, a 1-adamantyl group, an 2-adamantyl group, and a tricyclodecyl group.

The organic ammonium ion represented by A is preferably $CH_3NH_3^+$ (also referred to as a methylammonium ion), $C_2H_5NH_3^+$ (also referred to as an ethylammonium ion), or $C_3H_7NH_3^+$ (also referred to as a propylammonium ion), more preferably a methylammonium ion or an ethylammonium ion, and still more preferably a methylammonium ion.
(Amidinium ion)

Examples of the amidinium ion represented by A include an amidinium ion represented by the following formula (A4).

(A4)

In formula (A4), $R^{10}$ to $R^{13}$ each independently represent a hydrogen atom, an alkyl group, or a cycloalkyl group.

The alkyl groups represented by $R^{10}$ to $R^{13}$ may be each independently linear or branched. The alkyl groups represented by $R^{10}$ to $R^{13}$ may each independently have an amino group as a substituent.

The alkyl groups represented by $R^{10}$ to $R^{13}$ each independently usually have 1 to 20 carbon atoms, preferably have 1 to 4 carbon atoms, and more preferably have 1 to 3 carbon atoms.

The cycloalkyl groups represented by $R^{10}$ to $R^{13}$ may each independently have an amino group as a substituent.

The cycloalkyl groups represented by $R^{10}$ to $R^{13}$ each independently usually have 3 to 30 carbon atoms, preferably have 3 to 11 carbon atoms, and more preferably have 3 to 8 carbon atoms. The number of carbon atoms includes the number of carbon atoms of a substituent.

Specific examples of the alkyl groups of $R^{10}$ to $R^{13}$ each independently include the same groups as the alkyl groups exemplified for $R^6$ to $R^9$.

Specific examples of the cycloalkyl groups of $R^{10}$ to $R^{13}$ each independently include the same groups as the cycloalkyl groups exemplified for $R^6$ to $R^9$.

The groups represented by $R^{10}$ to $R^{13}$ are each independently preferably a hydrogen atom or an alkyl group.

By reducing the number of alkyl groups and cycloalkyl groups contained in formula (A4) and reducing the number of carbon atoms of the alkyl groups and the cycloalkyl groups, a perovskite compound having a three-dimensional structure with high emission intensity can be obtained.

In the amidinium ion, the total number of carbon atoms contained in the alkyl groups and the cycloalkyl groups represented by $R^{10}$ to $R^{13}$ is preferably 1 to 4. More preferably, $R^{10}$ is an alkyl group having one carbon atom, and $R^{11}$ to $R^{13}$ are hydrogen atoms.

In the perovskite compound, when A is a cesium ion, an organic ammonium ion having 3 or less carbon atoms, or an amidinium ion having 3 or less carbon atoms, the perovskite compound generally has a three-dimensional structure.

In the perovskite compound, when A is an organic ammonium ion having 4 or more carbon atoms or an amidinium ion having 4 or more carbon atoms, the perovskite compound has either or both of a two-dimensional structure and a quasi-two-dimensional structure. In this case, the perovskite compound can have the two-dimensional structure or the quasi-two-dimensional structure in a part or the whole of the crystal.

A structure obtained by stacking a plurality of two-dimensional perovskite type crystal structures is equivalent to a three-dimensional perovskite type crystal structure (reference document: P. PBoix et al., J. Phys. Chem. Lett. 2015, 6, 898-907 and the like).

The ionic radius of A is preferably 1.5 Å or more and 3.0 Å or less, more preferably 1.8 Å or more and 3.0 Å or less, and still more preferably 2.0 Å or more and 2.6 Å or less.

When the ionic radius of A is within the above range, the unit cell volume of (1) perovskite compound is easily controlled within a predetermined range.

Here, as the "ionic radius of A", a value calculated by a method described in a known literature (Chem. Sci., 2014, 5, 4712-4715) can be adopted.

In (1) perovskite compound, A may be used singly or in combination of two or more types thereof.

When A contains two or more types of monovalent cations, the ionic radii of all As contained in (1) perovskite compound are each preferably within the above range.
(Component B)

B constituting the perovskite compound may be one or more types of metal ions each having an ionic radius of 0.7 Å or more and 1.4 Å or less and selected from the group consisting of a monovalent metal ion, a divalent metal ion, and a trivalent metal ion.

B preferably contains a divalent metal ion, more preferably contains one or more types of metal ions selected from the group consisting of a lead ion (ionic radius: 1.19 Å), a tin ion (ionic radius: 0.93 Å), an antimony ion (ionic radius: 0.76 Å), a bismuth ion (ionic radius: 1.03 Å), and an indium ion (ionic radius: 0.800 Å), still more preferably contains a lead ion or a tin ion, and particularly preferably contains a lead ion.

The ionic radius of B is 0.7 Å or more and 1.4 Å or less, more preferably 0.8 Å or more and 1.3 Å or less, and still more preferably 0.9 Å or more and 1.2 Å or less.

When the ionic radius of B is within the above range, the unit cell volume of (1) perovskite compound is easily controlled within a predetermined range, defects in the crystal structure in the perovskite compound are reduced, and the quantum yield is improved.

Here, as the "ionic radius of B", a value of the ionic radius of Shannon in a divalent or trivalent state (when the ion can be a divalent ion and a trivalent ion, a divalent value is used) and in a six-coordination state can be used (reference document: R. D. Shannon, Acta Crystallogr., Sect. A, 32, 751 (1976)).

In (1) perovskite compound, B may be used singly or in combination of two or more types thereof.

When B contains two or more types of metal ions, the ionic radii of all Bs contained in (1) perovskite compound are each preferably within the above range.

(Component X)

X constituting the perovskite compound is at least one type of halide ion selected from the group consisting of halide ions each having an ionic radius of 0.5 Å or more and 2.5 Å or less.

Examples of the halide ion include a chloride ion (ionic radius: 1.81 Å), a bromide ion (ionic radius: 1.96 Å), a fluoride ion (ionic radius: 1.33 Å), and an iodide ion (ionic radius: 2.19 Å). X is preferably a bromide ion.

When the ionic radius of X is within the above range, the unit cell volume of (1) perovskite compound is easily controlled within a predetermined range, defects in the crystal structure in the perovskite compound are reduced, and the quantum yield is improved.

Here, as the "ionic radius of a halide ion", a value described in Encyclopedic dictionary of chemistry 7, compact edition, (Kyoritsu Shuppan Co., Ltd., issued on Sep. 15, 2006) can be adopted.

In (1) perovskite compound, X may be used singly or in combination of two or more types thereof.

When X contains two or more types of halide ions, the content ratio of the halide ions can be appropriately selected depending on an emission wavelength. For example, X can be formed of a combination of a bromide ion and a chloride ion, or a combination of a bromide ion and an iodide ion.

When X contains two or more types of halide ions, the ionic radii of all halide ions contained in (1) perovskite compound are each preferably within the above range.

X can be appropriately selected depending on a desired emission wavelength.

A perovskite compound containing a bromide ion as X can emit fluorescence having a maximum intensity peak in a wavelength range of usually 480 nm or more, preferably 500 nm or more, more preferably 520 nm or more.

The perovskite compound containing a bromide ion as X can emit fluorescence having a maximum intensity peak in a wavelength range of usually 700 nm or less, preferably 600 nm or less, more preferably 580 nm or less.

The above upper limit values and lower limit values of the wavelength range can be arbitrarily combined.

When X in the perovskite compound is a bromide ion, an emission peak of fluorescence is usually 480 to 700 nm, preferably 500 to 600 nm, and more preferably 520 to 580 nm.

A perovskite compound containing an iodide ion as X can emit fluorescence having a maximum intensity peak in a wavelength range of usually 520 nm or more, preferably 530 nm or more, more preferably 540 nm or more.

The perovskite compound containing an iodide ion as X can emit fluorescence having a maximum intensity peak in a wavelength range of usually 800 nm or less, preferably 750 nm or less, more preferably 730 nm or less.

The above upper limit values and lower limit values of the wavelength range can be arbitrarily combined.

When X in the perovskite compound is an iodide ion, an emission peak of fluorescence is usually 520 to 800 nm, preferably 530 to 750 nm, and more preferably 540 to 730 nm.

A perovskite compound containing a chloride ion as X can emit fluorescence having a maximum intensity peak in a wavelength range of usually 300 nm or more, preferably 310 nm or more, more preferably 330 nm or more.

The perovskite compound containing a chloride ion as X can emit fluorescence having a maximum intensity peak in a wavelength range of usually 600 nm or less, preferably 580 nm or less, more preferably 550 nm or less.

The above upper limit values and lower limit values of the wavelength range can be arbitrarily combined.

When X in the perovskite compound is a chloride ion, an emission peak of fluorescence is usually 300 to 600 nm, preferably 310 to 580 nm, and more preferably 330 to 550 nm.

(Examples of Perovskite Compound Having Three-Dimensional Structure)

Preferred examples of the perovskite compound having a three-dimensional structure represented by $ABX_{(3+\delta)}$ include $CH_3NH_3PbBr_3$, $CH_3NH_3PbCl_3$, $CH_3NH_3PbI_3$, $CH_3NH_3PbBr_{(3-y)}I_y$ ($0<y<3$), $CH_3NH_3PbBr_{(3-y)}Cl_y$ ($0<y<3$), $(H_2N=CH-NH_2)PbBr_3$, $(H_2N=CH-NH_2)PbCl_3$, and $(H_2N=CH-NH_2)PbI_3$.

Preferred examples of the perovskite compound having a three-dimensional structure also include $CH_3NH_3Pb_{(1-a)}Ca_aBr_3$ ($0<a\leq0.7$), $CH_3NH_3Pb_{(1-a)}Sr_aBr_3$ ($0<a\leq0.7$), $CH_3NH_3Pb_{(1-a)}La_aBr_{(3+\delta)}$ ($0<a\leq0.7$, $0<\delta\leq0.7$), $CH_3NH_3Pb_{(1-a)}Ba_aBr_3$ ($0<a\leq0.7$), and $CH_3NH_3Pb_{(1-a)}Dy_aBr_{(3+\delta)}$ ($0<a\leq0.7$, $0<\delta\leq0.7$).

Preferred examples of the perovskite compound having a three-dimensional structure also include $CH_3NH_3Pb_{(1-a)}Na_aBr_{(3+\delta)}$ ($0<a\leq0.7$, $-0.7\leq\delta<0$) and $CH_3NH_3Pb_{(1-a)}Li_aBr_{(3+\delta)}$ ($0<a\leq0.7$, $-0.7\leq\delta<0$).

Preferred examples of the perovskite compound having a three-dimensional structure also include $CsPb_{(1-a)}Na_aBr_{(3+\delta)}$ ($0<a\leq0.7$, $-0.7\leq\delta<0$) and $CsPb_{(1-a)}Li_aBr_{(3+\delta)}$ ($0<a\leq0.7$, $-0.7\leq\delta<0$).

Preferred examples of the perovskite compound having a three-dimensional structure also include $CH_3NH_3Pb_{(1-a)}Na_aBr_{(3+\delta-y)}I_y$ ($0<a\leq0.7$, $-0.7\leq\delta<0$, $0<y<3$), $CH_3NH_3Pb_{(1-a)}Li_aBr_{(3+\delta-y)}I_y$ ($0<a\leq0.7$, $-0.7\leq\delta<0$, $0<y<3$), $CH_3NH_3Pb_{(1-a)}Na_aBr_{(3+\delta-y)}Cl_y$ ($0<a\leq0.7$, $-0.7\leq\delta<0$, $0<y<3$), and $CH_3NH_3Pb_{(1-a)}Li_aBr_{(3+\delta-y)}Cl_y$ ($0<a\leq0.7$, $-0.7\leq\delta<0$, $0<y<3$).

Preferred examples of the perovskite compound having a three-dimensional structure also include $(H_2N=CH-NH_2)Pb_{(1-a)}Na_aBr_{(3+\delta)}$ ($0<a\leq0.7$, $-0.7\leq\delta<0$), $(H_2N=CH-NH_2)Pb_{(1-a)}Li_aBr_{(3+\delta)}$ ($0<a\leq0.7$, $-0.7\leq\delta<0$), $(H_2N=CH-NH_2)Pb_{(1-a)}Na_aBr_{(3+\delta-y)}I_y$ ($0<a\leq0.7$, $-0.7\leq\delta<0$, $0<y<3$), and $(H_2N=CH-NH_2)Pb_{(1-a)}Na_aBr_{(3+\delta-y)}Cl_y$ ($0<a\leq0.7$, $-0.7\leq\delta<0$, $0<y<3$).

Preferred examples of the perovskite compound having a three-dimensional structure also include $CsPbBr_3$, $CsPbCl_3$, $CsPbI_3$, $CsPbBr_{(3-y)}I_y$ ($0<y<3$), and $CsPbBr_{(3-y)}Cl_y$ ($0<y<3$).

Preferred examples of the perovskite compound having a three-dimensional structure also include $CH_3NH_3Pb_{(1-a)}Zn_aBr_3$ (0<a≤0.7), $CH_3NH_3Pb_{(1-a)}Al_aBr_{(3+\delta)}$ (0<a≤0.7, 0≤δ≤0.7), $CH_3NH_3Pb_{(1-a)}Co_aBr_3$ (0<a≤0.7), $CH_3NH_3Pb_{(1-a)}Mn_aBr_3$ (0<a≤0.7), and $CH_3NH_3Pb_{(1-a)}Mg_aBr_3$ (0<a≤0.7).

Preferred examples of the perovskite compound having a three-dimensional structure also include $CsPb_{(1-a)}Zn_aBr_3$ (0<a≤0.7), $CsPb_{(1-a)}Al_aBr_{(3+\delta)}$ (0<a≤0.7, 0<δ≤0.7), $CsPb_{(1-a)}Co_aBr_3$ (0<a≤0.7), $CsPb_{(1-a)}Mn_aBr_3$ (0<a≤0.7), and $CsPb_{(1-a)}Mg_aBr_3$ (0<a≤0.7).

Preferred examples of the perovskite compound having a three-dimensional structure also include $CH_3NH_3Pb_{(1-a)}Zn_aBr_{(3-y)}I_y$ (0<a≤0.7, 0<y<3), $CH_3NH_3Pb_{(1-a)}Al_aBr_{(3+\delta-y)}I_y$ (0<a≤0.7, 0<δ≤0.7, 0<y<3), $CH_3NH_3Pb_{(1-a)}Co_aBr_{(3-y)}I_y$ (0<a≤0.7, 0<y<3), $CH_3NH_3Pb_{(1-a)}Mn_aBr_{(3-y)}I_y$ (0<a≤0.7, 0<y<3), $CH_3NH_3Pb_{(1-a)}Mg_aBr_{(3-y)}I_y$ (0<a≤0.7, 0<y<3), $CH_3NH_3Pb_{(1-a)}Zn_aBr_{(3-y)}Cl_y$ (0<a≤0.7, 0<y<3), $CH_3NH_3Pb_{(1-a)}Al_aBr_{(3+\delta-y)}Cl_y$ (0<a≤0.7, 0<δ≤0.7, 0<y<3), $CH_3NH_3Pb_{(1-a)}Co_aBr_{(3+\delta-y)}Cl_y$ (0<a≤0.7, 0<δ≤0.7, 0<y<3), $CH_3NH_3Pb_{(1-a)}Mn_aBr_{(3-y)}Cl_y$ (0<a≤0.7, 0<y<3), and $CH_3NH_3Pb_{(1-a)}Mg_aBr_{(3-y)}Cl_y$ (0<a≤0.7, 0<y<3).

Preferred examples of the perovskite compound having a three-dimensional structure also include $(H_2N=CH-NH_2)Zn_aBr_3$ (0<a≤0.7), $(H_2N=CH-NH_2)Mg_aBr_3$ (0<a≤0.7), $(H_2N=CH-NH_2)Pb_{(1-a)}Zn_aBr_{(3-y)}I_y$ (0<a≤0.7, 0<y<3), and $(H_2N=CH-NH_2)Pb_{(1-a)}Zn_aBr_{(3-y)}Cl_y$ (0<a≤0.7, 0<y<3).

Among the above-described perovskite compounds each having a three-dimensional structure, $CsPbBr_3$, $CsPbBr_{(3-y)}I_y$ (0<y<3), and $(H_2N=CH-NH_2)PbBr_3$ are more preferable, and $(H_2N=CH-NH_2)PbBr_3$ is still more preferable.

(Examples of Perovskite Compound Having Two-Dimensional Structure)

Preferred examples of the perovskite compound having a two-dimensional structure include $(C_4H_9NH_3)_2PbBr_4$, $(C_4H_9NH_3)_2PbCl_4$, $(C_4H_9NH_3)_2PbI_4$, $(C_7H_{15}NH_3)_2PbBr_4$, $(C_7H_{15}NH_3)_2PbCl_4$, $(C_7H_{15}NH_3)_2PbI_4$, $(C_4H_9NH_3)_2Pb_{(1-a)}Li_aBr_{(4+\delta)}$ (0<a≤0.7, −0.7≤δ<0), $(C_4H_9NH_3)_2Pb_{(1-a)}Na_aBr^{(4+\delta)}$ (0<a≤0.7, −0.7≤δ<0), and $(C_4H_9NH_3)_2Pb_{(1-a)}Rb_aBr_{(4+\delta)}$ (0<a≤0.7, −0.7≤δ<0).

Preferred examples of the perovskite compound having a two-dimensional structure also include $(C_7H_{15}NH_3)_2Pb_{(1-a)}Na_aBr_{(4+\delta)}$ (0<a≤0.7, −0.7≤δ<0), $(C_7H_{15}NH_3)_2Pb_{(1-a)}Li_aBr_{(4+\delta)}$ (0<a≤0.7, −0.7≤δ<0), and $(C_7H_{15}NH_3)_2Pb_{(1-a)}Rb_aBr_{(4+\delta)}$ (0<a≤0.7, −0.7≤δ<0).

Preferred examples of the perovskite compound having a two-dimensional structure also include $(C_4H_9NH_3)_2Pb_{(1-a)}Na_aBr_{(4+\delta-y)}I_y$ (0<a≤0.7, −0.7≤δ<0, 0<y<4), $(C_4H_9NH_3)_2Pb_{(1-a)}Li_aBr_{(4+\delta-y)}I_y$ (0<a≤0.7, −0.7≤δ<0, 0<y<4), and $(C_4H_9NH_3)_2Pb_{(1-a)}Rb_aBr_{(4+\delta-y)}I_y$ (0<a≤0.7, −0.7≤δ<0, 0<y<4).

Preferred examples of the perovskite compound having a two-dimensional structure also include $(C_4H_9NH_3)_2Pb_{(1-a)}Na_aBr_{(4+\delta-y)}Cl_y$ (0<a≤0.7, −0.7≤δ<0, 0<y<4), $(C_4H_9NH_3)_2Pb_{(1-a)}Li_aBr_{(4+\delta-y)}Cl_y$ (0<a≤0.7, −0.7≤δ<0, 0<y<4), and $(C_4H_9NH_3)_2Pb_{(1-a)}Rb_aBr_{(4+\delta y)}Cl_y$ (0<a≤0.7, −0.7≤δ<0, 0<y<4).

Preferred examples of the perovskite compound having a two-dimensional structure also include $(C_4H_9NH_3)_2PbBr_4$ and $(C_7H_{15}NH_3)_2PbBr_4$.

Preferred examples of the perovskite compound having a two-dimensional structure also include $(C_4H_9NH_3)_2PbBr_{(4-y)}Cl_y$ (0<y<4) and $(C_4H_9NH_3)_2PbBr_{(4-y)}I_y$ (0<y<4).

Preferred examples of the perovskite compound having a two-dimensional structure also include $(C_4H_9NH_3)_2Pb_{(1-a)}Zn_aBr_4$ (0<a≤0.7), $(C_4H_9NH_3)_2Pb_{(1-a)}Mg_aBr_4$ (0<a≤0.7), $(C_4H_9NH_3)_2Pb_{(1-a)}Co_aBr_4$ (0<a≤0.7), and $(C_4H_9NH_3)_2Pb_{(1-a)}Mn_aBr_4$ (0<a≤0.7).

Preferred examples of the perovskite compound having a two-dimensional structure also include $(C_7H_{15}NH_3)_2Pb_{(1-a)}Zn_aBr_4$ (0<a≤0.7), $(C_7H_{15}NH_3)_2Pb_{(1-a)}Mg_aBr_4$ (0<a≤0.7), $(C_7H_{15}NH_3)_2Pb_{(1-a)}Co_aBr_4$ (0<a≤0.7), and $(C_7H_{15}NH_3)_2Pb_{(1-a)}Mn_aBr_4$ (0<a≤0.7).

Preferred examples of the perovskite compound having a two-dimensional structure also include $(C_4H_9NH_3)_2Pb_{(1-a)}Zn_aBr_{(4-y)}I_y$ (0<a≤0.7, 0<y<4), $(C_4H_9NH_3)_2Pb_{(1-a)}Mg_aBr_{(4-y)}I_y$ (0<a≤0.7, 0<y<4), $(C_4H_9NH_3)_2Pb_{(1-a)}Co_aBr_{(4-y)}I_y$ (0<a≤0.7, 0<y<4), and $(C_4H_9NH_3)_2Pb_{(1-a)}Mn_aBr_{(4-y)}I_y$ (0<a≤0.7, 0<y<4).

Preferred examples of the perovskite compound having a two-dimensional structure also include $(C_4H_9NH_3)_2Pb_{(1-a)}Zn_aBr_{(4-y)}Cl_y$ (0<a≤0.7, 0<y<4), $(C_4H_9NH_3)_2Pb_{(1-a)}Mg_aBr_{(4-y)}Cl_y$ (0<a≤0.7, 0<y<4), $(C_4H_9NH_3)_2Pb_{(1-a)}Co_aBr_{(4-y)}Cl_y$ (0<a≤0.7, 0<y<4), and $(C_4H_9NH_3)_2Pb_{(1-a)}Mn_aBr_{(4-y)}Cl_y$ (0<a≤0.7, 0<y<4).

<Particle Size of (1) Perovskite Compound>

The average particle size of (1) is not particularly limited, but is preferably 1 nm or more, more preferably 2 nm or more, and still more preferably 3 nm or more because the crystal structure can be maintained favorably.

In addition, the average particle size of (1) is preferably 10 μm or less, more preferably 1 μm or less, and still more preferably 500 nm or less because desired emission characteristics are easily maintained. Note that the term "emission characteristics" refers to optical characteristics of converted light obtained by irradiating (1) perovskite compound formed of light-emitting semiconductor particles with excitation light, such as quantum yield, emission intensity, and color purity. The color purity can be evaluated with a half width of a spectrum of converted light.

The upper limit values and the lower limit values of the average particle size of (1) can be arbitrarily combined.

For example, the average particle size of (1) is preferably 1 nm or more and 10 μm or less, more preferably 2 nm or more and 1 μm or less, and still more preferably 3 nm or more and 500 nm or less.

Here, the average particle size of (1) can be measured with, for example, a transmission electron microscope (hereinafter, also referred to as TEM) or a scanning electron microscope (hereinafter, also referred to a SEM). Specifically, the average particle size can be determined by measuring a maximum ferret diameter of 20 particles of (1) randomly selected with TEM or SEM, and calculating an average maximum ferret diameter, which is an arithmetic average value of the measured values.

Here, the term "maximum ferret diameter" means a maximum distance between two parallel straight lines sandwiching (1) on a TEM or SEM image.

<Composition 1>

Composition 1 of the present embodiment contains the above-described (1) perovskite compound and at least one compound selected from the group consisting of the following (2-1), a modified product of the following (2-1), the following (2-2), and a modified product of the following (2-2).

(2-1) Silazane (2-2) Silicon compound having at least one group selected from the group consisting of an amino group, an alkoxy group, and an alkylthio group Here, at least one compound selected from the group consisting of the (2-1), a modified product of the (2-1), the (2-2), and a modified product of the (2-2) may be collectively referred to as "(2) surface protecting agent".

Composition 1 of the present embodiment preferably contains the above-described (1) perovskite compound and at least one compound selected from the group consisting of the (2-1) and a modified product of the (2-1).

Composition 1 of the present embodiment may further contain at least one selected from the group consisting of the following (3), the following (4), and the following (5).
(3) Solvent
(4) Polymerizable compound
(5) Polymer <Composition 2>

Composition 2 of the present embodiment contains the above-described (1) perovskite compound and at least one selected from the group consisting of the (3), the (4), and the (5).

In the following description, (3) solvent, (4) polymerizable compound, and (5) polymer may be collectively referred to as "dispersion medium". In compositions 1 and 2 of the present embodiment, (1) perovskite compound may be dispersed in the dispersion medium.

Here, the term "dispersed" refers to a state in which (1) perovskite compound is floating in a dispersion medium, or a state in which (1) perovskite compound is suspended in a dispersion medium. When (1) perovskite compound is dispersed in a dispersion medium, a part of (1) perovskite compound may be precipitated.

Compositions 1 and 2 of the present embodiment may each further contain the following (6). Note that details of the following (6) will be described later.
(6) Surface modifier Compositions 1 and 2 of the present embodiment may each contain a component other than the above (1) to (6). For example, the composition of the present embodiment may further contain some impurities, a compound having an amorphous structure formed of elements constituting (1) perovskite compound, and a polymerization initiator.

Hereinafter, the above (2) to (6) contained in the composition of the present embodiment will be described.

<(2) Surface Protecting Agent>

Composition 1 of the present embodiment contains, as (2) surface protecting agent of (1) perovskite compound, at least one compound selected from the group consisting of (2-1) silazane, a modified product of the (2-1), (2-2) a silicon compound having at least one group selected from the group consisting of an amino group, an alkoxy group, and an alkylthio group, and a modified product of the (2-2).

Composition 1 of the present embodiment has an effect that (2) surface protecting agent covers a surface of (1) perovskite compound, thereby improving a quantum yield and shortening an emission wavelength.

<(2-1) Silazane>

(2-1) Silazane is a compound having a Si—N—Si bond. The silazane may be linear, branched, or cyclic.

The silazane may be a low molecular weight silazane or a high molecular weight silazane. Here, the high molecular weight silazane may be referred to as a polysilazane.

Here, the term "low molecular weight" means that the number average molecular weight is less than 600. Here, the term "high molecular weight" means that the number average molecular weight is 600 or more and 2000 or less.

Here, the term "number average molecular weight" means a value in terms of polystyrene, measured by a gel permeation chromatography (GPC) method.

(2-1-1. Low Molecular Weight Silazane)

The low molecular weight silazane is preferably, for example, a disilazane represented by the following formula (B1).

[Chemical Formula 2]

[Chemical formula 2]

(B1)

In formula (B1), $R^{14}$ and $R^{15}$ each independently represent a hydrogen atom, an alkyl group having 1 to 20 carbon atoms, an alkenyl group having 1 to 20 carbon atoms, a cycloalkyl group having 3 to 20 carbon atoms, an aryl group having 6 to 20 carbon atoms, or an alkylsilyl group having 1 to 20 carbon atoms.

$R^{14}$ and $R^{15}$ may each have a substituent such as an amino group. The plurality of $R^{15}$s may be the same as or different from each other.

Examples of the low molecular weight silazane represented by formula (B1) include 1,3-divinyl-1,1,3,3-tetramethyldisilazane, 1,3-diphenyltetramethyldisilazane, and 1,1,1,3,3,3-hexamethyldisilazane.

(2-1-2. Low Molecular Weight Silazane)

The low molecular weight silazane is also preferably, for example, a low molecular weight silazane represented by the following formula (B2).

[Chemical formula 3]

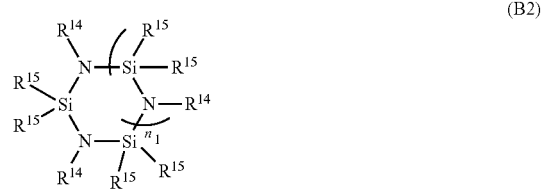

(B2)

In formula (B2), $R^{14}$ and $R^{15}$ are similar to $R^{14}$ and $R^{15}$ in the above formula (B1), respectively.

The plurality of $R^{14}$s may be the same as or different from each other.

The plurality of $R^{15}$s may be the same as or different from each other.

In formula (B2), $n_1$ represents an integer of 1 or more and 20 or less. $n_1$ may be an integer of 1 or more and 10 or less, and may be 1 or 2.

Examples of the low molecular weight silazane represented by formula (B2) include octamethylcyclotetrasilazane, 2,2,4,4,6,6-hexamethylcyclotrisilazane, and 2,4,6-trimethyl-2,4,6-trivinylcyclotrisilazane.

The low molecular weight silazane is preferably octamethylcyclotetrasilazane or 1,3-diphenyltetramethyldisilazane, and more preferably octamethylcyclotetrasilazane.

(2-1-3. High Molecular Weight Silazane)

The high molecular weight silazane is preferably, for example, a high molecular weight silazane (polysilazane) represented by the following formula (B3).

The polysilazane is a polymer compound having a Si—N—Si bond. There may be one or more types of constituent units of the polysilazane represented by formula (B3).

[Chemical formula 4]

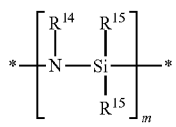

(B3)

In formula (B3), $R^{14}$ and $R^{15}$ are similar to $R^{14}$ and $R^{15}$ in the above formula (B1), respectively.

In formula (B3), * represents a bond. $R^{14}$ is bonded to a bond of the N atom at an end of the molecular chain.

$R^{15}$ is bonded to a bond of the Si atom at an end of the molecular chain.

The plurality of $R^{14}$s may be the same as or different from each other.

The plurality of $R^{15}$s may be the same as or different from each other.

m represents an integer of 2 or more and 10000 or less.

The polysilazane represented by formula (B3) may be, for example, a perhydropolysilazane in which all of $R^{14}$s and $R^{15}$s are hydrogen atoms.

The polysilazane represented by formula (B3) may be, for example, an organopolysilazane in which at least one $R^{15}$ is a group other than a hydrogen atom. The perhydropolysilazane or the organopolysilazane may be appropriately selected depending on an application, and the perhydropolysilazane and the organopolysilazane may be mixed to be used.

The composition of the present embodiment preferably contains an organopolysilazane represented by formula (B3) from a viewpoint of improving the dispersibility of (1) and enhancing an effect of suppressing aggregation.

The organopolysilazane represented by formula (B3) may be, for example, an organopolysilazane in which at least one of $R^{14}$ and $R^{15}$ is an alkyl group having 1 to 20 carbon atoms, an alkenyl group having 1 to 20 carbon atoms, a cycloalkyl group having 3 to 20 carbon atoms, an aryl group having 6 to 20 carbon atoms, or an alkylsilyl group having 1 to 20 carbon atoms.

Among the organopolysilazanes, an organopolysilazane which is represented by formula (B3) and in which at least one of $R^{14}$ and $R^{15}$ is a methyl group is preferable.

(2-1-4. High Molecular Weight Silazane)

The high molecular weight silazane is also preferably, for example, a polysilazane having a structure represented by the following formula (B4).

The polysilazane may have a ring structure in a part of the molecule, and may have, for example, the structure represented by formula (B4).

[Chemical formula 5]

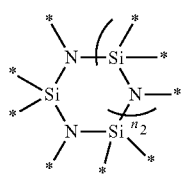

(B4)

In formula (B4), * represents a bond.

The bond in formula (B4) may be bonded to a bond of the polysilazane represented by formula (B3) or a bond of a constituent unit of the polysilazane represented by formula (B3).

When the polysilazane contains a plurality of structures each represented by formula (B4) in the molecule, a bond of a structure represented by formula (B4) may be directly bonded to a bond of another structure represented by formula (B4).

$R^{14}$ is bonded to a bond of an N atom not bonded to any one of a bond of the polysilazane represented by formula (B3), a bond of a constituent unit of the polysilazane represented by formula (B3), and a bond of another structure represented by formula (B4).

$R^{15}$ is bonded to a bond of a Si atom not bonded to any one of a bond of the polysilazane represented by formula (B3), a bond of a constituent unit of the polysilazane represented by formula (B3), and a bond of another structure represented by formula (B4).

$n_2$ represents an integer of 1 or more and 10000 or less. $n_2$ may be an integer of 1 or more and 10 or less, and may be 1 or 2.

The composition of the present embodiment preferably contains an organopolysilazane having a structure represented by formula (B4) from a viewpoint of improving the dispersibility of (1) and enhancing an effect of suppressing aggregation.

The organopolysilazane having a structure represented by formula (B4) may be, for example, an organopolysilazane in which at least one bond is bonded to $R^{14}$ or $R^{15}$, and at least one of the $R^{14}$ and $R^{15}$ is an alkyl group having 1 to 20 carbon atoms, an alkenyl group having 1 to 20 carbon atoms, a cycloalkyl group having 3 to 20 carbon atoms, an aryl group having 6 to 20 carbon atoms, or an alkylsilyl group having 1 to 20 carbon atoms.

Among the organopolysilazanes, a polysilazane which contains a structure represented by formula (B4) and in which at least one bond is bonded to $R^{14}$ or $R^{15}$, and at least one of the $R^{14}$ and $R^{15}$ is a methyl group is preferable.

A general polysilazane has, for example, a structure in which a linear structure and a ring structure such as a 6-membered ring or an 8-membered ring are present, that is, the structure represented by the formula (B3) or (B4). A general polysilazane has a number average molecular weight (Mn) of about 600 to 2000 (in terms of polystyrene), and can be a liquid or solid substance depending on the molecular weight.

For the polysilazane, a commercially available product may be used, and examples of the commercially available product include NN120-10, NN120-20, NAX120-20, NN110, NAX120, NAX110, NL120A, NL110A, NL150A, NP110, NP140 (manufactured by AZ Electronic Materials Co., Ltd.), AZNN-120-20, Durazane (registered trademark) 1500 Slow Cure, Durazane1500 Rapid Cure, Durazane1800, and Durazane1033 (manufactured by Merck Performance Materials Co., Ltd.).

The polysilazane is preferably AZNN-120-20, Durazane1500 Slow Cure, or Durazane1500 Rapid Cure, and more preferably Durazane1500 Slow Cure.

<Modified Product of (2-1) Silazane>

Here, the term "modification" means that a silicon compound having a Si—N bond, a Si—SR bond (R is a hydrogen atom or an organic group), or a Si—OR bond (R is a hydrogen atom or an organic group) is hydrolyzed to generate a silicon compound having a Si—O—Si bond. The Si—O—Si bond may be generated by an intermolecular condensation reaction or an intramolecular condensation reaction.

Here, the term "modified product" refers to a compound obtained by modifying a silicon compound having a Si—N bond, a Si—SR bond, or a Si—OR bond.

The modified product of (2-1) is particularly preferably a modified product of a disilazane represented by the formula (B1), a modified product of a low molecular weight silazane represented by the formula (B2), a modified product of a polysilazane represented by the formula (B3), or a modified product of a polysilazane having a structure represented by the formula (B4) in a molecule thereof.

In the modified product of the low molecular weight silazane represented by formula (B2), the ratio of silicon atoms not bonded to nitrogen atoms with respect to all silicon atoms contained in the modified product of the low molecular weight silazane represented by formula (B2) is preferably 0.1 to 100%. The ratio of silicon atoms not bonded to nitrogen atoms is more preferably 10 to 98%, and still more preferably 30 to 95%.

Note that the "ratio of silicon atoms not bonded to nitrogen atoms" is determined by ((Si (mol))−(N (mol)) in Si—N bond))/Si (mol)×100 using measured values described later. Considering a modification reaction, the term "ratio of silicon atoms not bonded to nitrogen atoms" means "the ratio of silicon atoms contained in a siloxane bond generated by a modification treatment".

In the modified product of the polysilazane represented by formula (B3), the ratio of silicon atoms not bonded to nitrogen atoms with respect to all silicon atoms contained in the modified product of the polysilazane represented by formula (B3) is preferably 0.1 to 100%. The ratio of silicon atoms not bonded to nitrogen atoms is more preferably 10 to 98%, and still more preferably 30 to 95%.

In the modified product of the polysilazane having a structure represented by formula (B4), the ratio of silicon atoms not bonded to nitrogen atoms with respect to all silicon atoms contained in the modified product of the polysilazane having a structure represented by formula (B4) is preferably 0.1 to 99%. The ratio of silicon atoms not bonded to nitrogen atoms is more preferably 10 to 97%, and still more preferably 30 to 95%.

The number of Si atoms and the number of Si—N bonds in the modified product can be measured by X-ray photoelectron spectroscopy (XPS).

For the modified product, the "ratio of silicon atoms not bonded to nitrogen atoms" determined by using the values measured by the above method is preferably 0.1 to 99%, more preferably 10 to 99%, and still more preferably 30 to 95%.

<(2-2) Silicon Compound Having at Least One Group Selected from the Group Consisting of an Amino Group, an Alkoxy Group, and an Alkylthio Group>

Composition 1 of the present embodiment may contain (2-2) a silicon compound having at least one group selected from the group consisting of an amino group, an alkoxy group, and an alkylthio group. Hereinafter, (2-2) a silicon compound having at least one group selected from the group consisting of an amino group, an alkoxy group, and an alkylthio group may be collectively referred to as "(2-2) silicon compound".

Examples of (2-2) silicon compound include 3-aminopropyltriethoxysilane, 3-aminopropyltrimethoxysilane, dodecyltrimethoxysilane, trimethoxyphenylsilane, 1H,1H,2H,2H-perfluorooctyltriethoxysilane, trimethoxy (1H,1H,2H,2H-nonafluorohexyl) silane, 3-mercaptopropyltrimethoxysilane, and 3-mercaptopropyltriethoxysilane.

Among the compounds, 3-aminopropyltriethoxysilane, 3-aminopropyltrimethoxysilane, and trimethoxyphenylsilane are preferable, 3-aminopropyltriethoxysilane and 3-aminopropyltrimethoxysilane are more preferable, and 3-aminopropyltrimethoxysilane is still more preferable from a viewpoint of the durability of (1).

<Modified Product of (2-2) Silicon Compound>

The modified product of (2-2) silicon compound refers to a compound obtained by modifying the above-described (2-2) silicon compound. The "modification" is similar to that described in the modified product of (2-1) silazane.

In composition 1 of the present embodiment, the above-described (2) surface protecting agents may be used singly or in combination of two or more types thereof.

<(6) Surface Modifier>

A surface of (1) perovskite compound of the present embodiment may be covered with a surface modifier layer. The surface modifier layer may be located between (1) perovskite compound and (2) surface protecting agent.

Note that the form in which the surface modifier layer covers a "surface" of (1) perovskite compound includes, in addition to a form in which the surface modifier layer covers (1) perovskite compound in direct contact with (1) perovskite compound, a form in which the surface modifier layer is formed in direct contact with a surface of another layer formed on the surface of (1) perovskite compound and covers (1) perovskite compound without direct contact with the surface of (1) perovskite compound.

<Surface Modifier Layer>

The surface modifier layer contains, at least one ion or compound selected from the group consisting of an ammonium ion, an amine, primary to quaternary ammonium cations, an ammonium salt, a carboxylic acid, a carboxylate ion, and a carboxylate salt.

Among the ions and compounds, the surface modifier layer preferably contains at least one selected from the group consisting of an amine and a carboxylic acid.

Hereinafter, the material for forming the surface modifier layer may be referred to as "(6) surface modifier".

The surface modifier is a compound having an effect of covering a surface of (1) perovskite compound and stably dispersing (1) perovskite compound in the composition of the present embodiment when the composition is manufactured by a manufacturing method described later.

<Ammonium Ion, Primary to Quaternary Ammonium Cations, and Ammonium Salt>

The ammonium ion and primary to quaternary ammonium cations, which are (6) surface modifiers, are represented by the following formula (A1). The ammonium salt, which is (6) surface modifier, is a salt containing an ion represented by the following formula (A1).

[Chemical formula 6]

(A1)

In the ion represented by formula (A1), $R^1$ to $R^4$ each represent a hydrogen atom or a monovalent hydrocarbon group.

The hydrocarbon groups represented by $R^1$ to $R^4$ may be each a saturated hydrocarbon group or an unsaturated hydrocarbon group. Examples of the saturated hydrocarbon group include an alkyl group and a cycloalkyl group.

The alkyl groups represented by $R^1$ to $R^4$ may be linear or branched.

The number of carbon atoms of the alkyl group represented by each of $R^1$ to $R^4$ is usually 1 to 20, preferably 5 to 20, and more preferably 8 to 20.

The number of carbon atoms of the cycloalkyl group is usually 3 to 30, preferably 3 to 20, and more preferably 3 to 11. The number of carbon atoms includes the number of carbon atoms of a substituent.

The unsaturated hydrocarbon group of each of $R^1$ to $R^4$ may be linear or branched.

The number of carbon atoms of the unsaturated hydrocarbon group of each of $R^1$ to $R^4$ is usually 2 to 20, preferably 5 to 20, and more preferably 8 to 20.

Each of $R^1$ to $R^4$ is preferably a hydrogen atom, an alkyl group, or an unsaturated hydrocarbon group. The unsaturated hydrocarbon group is preferably an alkenyl group. Each of $R^1$ to $R^4$ is preferably an alkenyl group having 8 to 20 carbon atoms.

Specific examples of the alkyl groups of $R^1$ to $R^4$ include the alkyl groups exemplified for $R^6$ to $R^9$.

Specific examples of the cycloalkyl groups of $R^1$ to $R^4$ include the cycloalkyl groups exemplified for $R^6$ to $R^9$.

Examples of the alkenyl groups of $R^1$ to $R^4$ include the linear or branched alkyl groups exemplified for $R^6$ to $R^9$, in which any one single bond (C—C) between carbon atoms is replaced with a double bond (C=C), and the position of the double bond is not limited.

Preferred examples of the alkenyl groups of $R^1$ to $R^4$ include an ethenyl group, a propenyl group, a 3-butenyl group, a 2-butenyl group, a 2-pentenyl group, a 2-hexenyl group, a 2-nonenyl group, a 2-dodecenyl group, and a 9-octadecenyl group.

When the ammonium cation represented by formula (A1) forms a salt, a counter anion is not particularly limited. The counter anion is preferably a halide ion, a carboxylate ion, or the like. Examples of the halide ion include a bromide ion, a chloride ion, an iodide ion, and a fluoride ion.

Preferred examples of the ammonium salt having the ammonium cation represented by formula (A1) and a counter anion include a n-octyl ammonium salt and an oleyl ammonium salt.

<Amine>

The amine which is a surface modifier can be represented by the following formula (A11).

[Chemical formula 7]

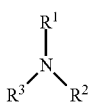

(A11)

In the above formula (A11), $R^1$ to $R^3$ represent the same groups as $R^1$ to $R^3$ included in the above formula (A1), respectively. However, at least one of $R^1$ to $R^3$ is a monovalent hydrocarbon group.

The amine which is a surface modifier may be any of primary and tertiary amines, but is preferably a primary or secondary amine, and more preferably a primary amine.

The amine which is a surface modifier is preferably an oleylamine.

<Carboxylic Acid, Carboxylate Ion, and Carboxylate Salt>

The carboxylate ion which is a surface modifier is represented by the following formula (A2). The carboxylate salt which is a surface modifier is a salt containing an ion represented by the following formula (A2).

$R^5$—$CO_2^-$ (A2)

Examples of the carboxylic acid which is a surface modifier include a carboxylic acid in which a proton ($H^+$) is bonded to a carboxylate anion represented by the above (A2).

In the ion represented by formula (A2), $R^5$ represents a monovalent hydrocarbon group. The hydrocarbon group represented by $R^5$ may be a saturated hydrocarbon group or an unsaturated hydrocarbon group. Examples of the saturated hydrocarbon group include an alkyl group and a cycloalkyl group.

The alkyl group represented by $R^5$ may be linear or branched.

The number of carbon atoms of the alkyl group represented by $R^5$ is usually 1 to 20, preferably 5 to 20, and more preferably 8 to 20.

The number of carbon atoms of the cycloalkyl group is usually 3 to 30, preferably 3 to 20, and more preferably 3 to 11. The number of carbon atoms also includes the number of carbon atoms of a substituent.

The unsaturated hydrocarbon group represented by $R^5$ may be linear or branched.

The number of carbon atoms of the unsaturated hydrocarbon group represented by $R^5$ is usually 2 to 20, preferably 5 to 20, and more preferably 8 to 20.

$R^5$ is preferably an alkyl group or an unsaturated hydrocarbon group. The unsaturated hydrocarbon group is preferably an alkenyl group.

Specific examples of the alkyl group of $R^5$ include the alkyl groups exemplified for $R^6$ to $R^9$.

Specific examples of the cycloalkyl groups of $R^5$ include the cycloalkyl groups exemplified for $R^6$ to $R^9$.

Specific examples of the alkenyl group of $R^5$ include the alkenyl groups exemplified for $R^1$ to $R^4$.

The carboxylate anion represented by formula (A2) is preferably an oleate anion.

When the carbokylate anion forms a salt, a counter cation is not particularly limited, but preferred examples thereof include an alkali metal cation, an alkaline earth metal cation, and an ammonium cation.

The carboxylic acid which is a surface modifier is preferably oleic acid.

Among the above-described surface modifiers, an ammonium salt, an ammonium ion, primary to quaternary ammonium cations, a carboxylate salt, and a carboxylate ion are preferable.

Among ammonium salts and ammonium ions, an oleylamine salt and an oleylammonium ion are more preferable.

Among carboxylate salts and carboxylate ions, an oleate and an oleate cation are more preferable.

In compositions 1 and 2 of the present embodiment, the above-described (6) surface modifiers may be used singly or in combination of two or more types thereof.

<(3) Solvent>

The solvent contained in the composition of the present embodiment is not particularly limited as long as the solvent is a medium that can disperse (1) perovskite compound of the present embodiment. The solvent contained in the composition of the present embodiment is preferably a solvent that hardly dissolves (1) perovskite compound of the present embodiment.

Here, the term "solvent" refers to a substance that is in a liquid state at 1 atm and 25° C. However, the solvent does not include a polymerizable compound described later.

Examples of the solvent include the following (a) to (k).

(a) Ester
(b) Ketone
(c) Ether
(d) Alcohol
(e) Glycol ether
(f) Organic solvent having an amide group
(g) Organic solvent having a nitrile group
(h) Organic solvent having a carbonate group
(i) Halogenated hydrocarbon
(j) Hydrocarbon
(k) Dimethyl sulfoxide Examples of (a) ester include methyl formate, ethyl formate, propyl formate, pentyl formate, methyl acetate, ethyl acetate, and pentyl acetate.

Examples of (b) ketone include γ-butyrolactone, N-methyl-2-pyrrolidone, acetone, diisobutyl ketone, cyclopentanone, cyclohexanone, and methylcyclohexanone.

Examples of (c) ether include diethyl ether, methyl-tert-butyl ether, diisopropyl ether, dimethoxymethane, dimethoxyethane, 1,4-dioxane, 1,3-dioxolane, 4-methyldioxolane, tetrahydrofuran, methyl tetrahydrofuran, anisole, and phenetol.

Examples of (d) alcohol include methanol, ethanol, 1-propanol, 2-propanol, 1-butanol, 2-butanol, tert-butanol, 1-pentanol, 2-methyl-2-butanol, methoxypropanol, diacetone alcohol, cyclohexanol, 2-fluoroethanol, 2,2,2-trifluoroethanol, and 2,2,3,3-tetrafluoro-1-propanol.

Examples of (e) glycol ether include ethylene glycol monomethyl ether, ethylene glycol monoethyl ether, ethylene glycol monobutyl ether, ethylene glycol monoethyl ether acetate, and triethylene glycol dimethyl ether.

Examples of (f) organic solvent having an amide group include N,N-dimethylformamide, acetamide, and N,N-dimethylacetamide.

Examples of (g) organic solvent having a nitrile group include acetonitrile, isobutyronitrile, propionitrile, and methoxynitrile.

Examples of (h) organic solvent having a carbonate group include ethylene carbonate and propylene carbonate.

Examples of (i) halogenated hydrocarbon include methylene chloride and chloroform.

Examples of (j) hydrocarbon include n-pentane, cyclohexane, n-hexane, 1-octadecene, benzene, toluene, and xylene.

Among these solvents, (a) ester, (b) ketone, (c) ether, (g) organic solvent having a nitrile group, (h) organic solvent having a carbonate group, (i) halogenated hydrocarbon, and (j) hydrocarbon are preferable because these have low polarity and are considered to hardly dissolve (1) perovskite compound of the present embodiment.

Furthermore, the solvent used for the composition of the present embodiment is more preferably (i) halogenated hydrocarbon or (j) hydrocarbon.

In compositions 1 and 2 of the present embodiment, the above-described solvents may be used singly or in combination of two or more types thereof.

<(4) Polymerizable Compound>

The polymerizable compound contained in the composition of the present embodiment is preferably a polymerizable compound that hardly dissolves (1) perovskite compound of the present embodiment at a temperature at which the composition of the present embodiment is manufactured.

Here, the term "polymerizable compound" means a monomer compound (monomer) having a polymerizable group. Examples of the polymerizable compound include a monomer that is in a liquid state at 1 atm and 25° C.

For example, when the composition is manufactured at normal temperature and under normal pressure, the polymerizable compound is not particularly limited. Examples of the polymerizable compound include known polymerizable compounds such as styrene, an acrylate, a methacrylate, and acrylonitrile. Among these compounds, the polymerizable compound is preferably either one or both of an acrylate and a methacrylate, which are monomers of acrylic resins.

In compositions 1 and 2 of the present embodiment, the polymerizable compounds may be used singly or in combination of two or more types thereof.

In the composition of the present embodiment, the ratio of the total amount of an acrylate and a methacrylate with respect to all (4) polymerizable compounds may be 10 mol % or more. The ratio may be 30 mol % or more, 50 mol % or more, 80 mol % or more, or 100 mol %.

<(5) Polymer>

The polymer contained in the composition of the present embodiment is preferably a polymer having low solubility of (1) perovskite compound of the present embodiment at a temperature at which the composition of the present embodiment is manufactured.

For example, when the composition is manufactured at normal temperature and under normal pressure, the polymer is not particularly limited, but examples thereof include known polymers such as polystyrene, an acrylic resin, and an epoxy resin. Among these compounds, the polymer is preferably an acrylic resin. The acrylic resin contains either one or both of a constituent unit derived from an acrylate and a constituent unit derived from a methacrylate.

In the composition of the present embodiment, the ratio of the total amount of the constituent unit derived from an acrylate and the constituent unit derived from a methacrylate with respect to all the constituent units contained in (5) polymer may be 10 mol % or more. The ratio may be 30 mol % or more, 50 mol % or more, 80 mol % or more, or 100 mol %.

The weight average molecular weight of (5) polymer is preferably 100 to 1,200,000, more preferably 1,000 to 800,000, and still more preferably 5,000 to 150,000.

Here, the term "weight average molecular weight" means a value in terms of polystyrene, measured by a gel permeation chromatography (GPC) method.

In compositions 1 and 2 of the present embodiment, the above-described polymers may be used singly or in combination of two or more types thereof.

<Content of Each Component in Composition>

In compositions 1 and 2 of the present embodiment, the content ratio of (1) perovskite compound with respect to the total mass of the composition is not particularly limited.

The content ratio is preferably 90% by mass or less, more preferably 40% by mass or less, still more preferably 10% by mass or less, and particularly preferably 3% by mass or less from a viewpoint of preventing concentration quenching.

In addition, the content ratio is preferably 0.0002% by mass or more, more preferably 0.002% by mass or more, and still more preferably 0.01% by mass or more from a viewpoint of obtaining a favorable quantum yield.

The above upper limit values and lower limit values can be arbitrarily combined.

The content ratio of (1) perovskite compound with respect to the total mass of the composition is usually 0.0002 to 90% by mass.

The content ratio of (1) perovskite compound with respect to the total mass of the composition is preferably 0.001 to 40% by mass, more preferably 0.002 to 10% by mass, and still more preferably 0.01 to 3% by mass.

A composition in which the content ratio of (1) perovskite compound with respect to the total mass of the composition is within the above range is preferable because (1) perovskite compound is less likely to aggregate and a light-emitting property is exhibited favorably.

In composition 1 of the present embodiment, the content ratio of (2) surface protecting agent with respect to the total mass of the composition is not particularly limited.

The content ratio is preferably 30% by mass or less, more preferably 10% by mass or less, and still more preferably 7.5% by mass or less from a viewpoint of improving the dispersibility of (1) perovskite compound and improving durability.

In addition, the content ratio is preferably 0.001% by mass or more, more preferably 0.01% by mass or more, and still more preferably 0.1% by mass or more from a viewpoint of improving durability.

The above upper limit values and lower limit values can be arbitrarily combined.

The content ratio of (2) surface protecting agent with respect to the total mass of the composition is usually 0.001 to 30% by mass.

The content ratio of (2) surface protecting agent with respect to the total mass of the composition is preferably 0.001 to 30% by mass, more preferably 0.001 to 10% by mass, and still more preferably 0.1 to 7.5% by mass.

In compositions 1 and 2 of the present embodiment, the content ratio of the dispersion medium with respect to the total mass of the composition is not particularly limited.

The content ratio is preferably 99.99% by mass or less, more preferably 99.9% by mass or less, and still more preferably 99% by mass or less from a viewpoint of improving the dispersibility of (1) perovskite compound and improving durability.

In addition, the content ratio is preferably 0.1% by mass or more, more preferably 1% by mass or more, still more preferably 10% by mass or more, further still more preferably 50% by mass or more, further still more preferably 80% by mass or more, and most preferably 90% by mass or more from a viewpoint of improving durability.

The above upper limit values and lower limit values can be arbitrarily combined.

The content ratio of the dispersion medium with respect to the total mass of the composition is usually 0.1 to 99.99% by mass.

The content ratio of the dispersion medium with respect to the total mass of the composition is preferably 1 to 99% by mass, more preferably 10 to 99% by mass, still more preferably 20 to 99% by mass, particularly preferably 50 to 99% by mass, and most preferably 90 to 99% by mass.

In the composition, the total content ratio of (1) perovskite compound, (2) surface protecting agent, and the dispersion medium may be 90% by mass or more, 95% by mass or more, 99% by mass or more, or 100% by mass with respect to the total mass of the composition.

In compositions 1 and 2 of the present embodiment, the content ratio of (6) surface modifier with respect to the total mass of the composition is not particularly limited.

The content ratio is preferably 30% by mass or less, more preferably 1% by mass or less, and still more preferably 0.1% by mass or less from a viewpoint of improving durability.

In addition, the content ratio is preferably 0.0001% by mass or more, more preferably 0.001% by mass or more, and still more preferably 0.01% by mass or more from a viewpoint of improving thermal durability.

The above upper limit values and lower limit values can be arbitrarily combined.

The content ratio of (6) surface modifier with respect to the total mass of the composition is usually 0.0001 to 30% by mass.

The content ratio of (6) surface modifier with respect to the total mass of the composition is preferably 0.001 to 1% by mass, and more preferably 0.01 to 0.1% by mass.

A composition in which the content ratio of (6) surface modifier with respect to the total mass of the composition is within the above range is preferable from a viewpoint of excellent thermal durability.

The total content ratio of some impurities, the compound having an amorphous structure formed of elements constituting (1) perovskite compound, and the polymerization initiator in the composition of the present embodiment is preferably 10% by mass or less, more preferably 5% by mass or less, and still more preferably 1% by mass or less with respect to the total mass of the composition.

<Blending Ratio of Each Component>

In compositions 1 and 2 of the present embodiment, a mass ratio of (1) perovskite compound to the dispersion medium [(1) perovskite compound/dispersion medium] may be 0.00001 to 10, 0.0001 to 5, or 0.0005 to 3.

A composition in which the blending ratio between (1) perovskite compound and the dispersion medium is within the above range is preferable because (1) perovskite compound is less likely to aggregate and emits light favorably.

In composition 1 of the present embodiment, a blending ratio between (1) perovskite compound and (2) surface protecting agent can be appropriately determined depending on the types of (1) and (2) and the like.

In composition 1 of the present embodiment, a molar ratio [Si/B] between a metal ion which is component B of (1) perovskite compound and the Si element of (2) surface protecting agent may be 0.001 to 200 or 0.01 to 50.

In composition 1 of the present embodiment, when (2) surface protecting agent is a modified product of a silazane represented by formula (B1) or (B2), a molar ratio [Si/B] between a metal ion which is component B of (1) perovskite compound and Si of a modified product of (2-1) silazane may be 0.001 to 100, 0.001 to 50, or 1 to 20.

In composition 1 of the present embodiment, when (2) surface protecting agent is a polysilazane having a constituent unit represented by formula (B3), a molar ratio [Si/B] between a metal ion which is component B of (1) perovskite compound and the Si element of a modified product of (2-1) silazane may be 0.001 to 100, 0.01 to 100, 0.1 to 100, 1 to 50, or 1 to 20.

A composition in which the blending ratio between (1) perovskite compound and (2) surface protecting agent is within the above range is preferable because (2) surface protecting agent particularly favorably exhibits an effect of improving durability against water vapor.

The molar ratio [Si/B] between the metal ion which is component B of the perovskite compound and the Si element of (2) surface protecting agent can be determined by the following method.

The number of moles (B) of metal ions as component B of the perovskite compound is determined by calculating the mass of the metal which is component B contained in the perovskite compound by inductively coupled plasma mass spectrometry (ICP-MS) and then converting the mass into moles. The number of moles (Si) of the Si element of (2) surface protecting agent is determined by performing molar conversion from the mass of (2) surface protecting agent used.

At this time, a ratio between the number of moles (Si) of the Si element of (2) surface protecting agent and the number of moles (B) of the metal ion which is component B of the perovskite compound is [Si/B].

In the composition of the present embodiment, the mass of (2) surface protecting agent with respect to the mass of (1) perovskite compound is preferably 1.1 parts by mass or more, more preferably 1.5 parts by mass or more, and still more preferably 1.8 parts by mass or more from a viewpoint of sufficiently improving a quantum yield. In addition, the mass of (2) surface protecting agent with respect to the mass of (1) perovskite compound is preferably 10 parts by mass or less, more preferably 4.9 parts by mass or less, and still more preferably 2.5 parts by mass or less.

The above upper limit values and lower limit values can be arbitrarily combined.

<Method for Manufacturing (1) Perovskite Compound>

(1) Perovskite compound can be manufactured by a method described below with reference to known documents (Nano Lett. 2015, 15, 3692-3696 and ACS Nano, 2015, 9, 4533-4542).

(First Manufacturing Method)

Examples of the method for manufacturing the perovskite compound include a manufacturing method including a step of dissolving component B, component X, and component A, which constitute the perovskite compound, in the above-described high-temperature (3) solvent to obtain a solution, and a step of cooling the solution.

Hereinafter, the first manufacturing method will be specifically described.

First, a compound containing component B and component X and a compound containing component A are dissolved in the high-temperature (3) solvent to obtain a solution. The "compound containing component A" may contain component X.

In this step, the compounds may be added to the high-temperature (3) solvent and dissolved to obtain a solution.

In addition, in this step, the compounds may be added to (3) solvent, and then the temperature may be raised to obtain a solution. In the first manufacturing method, the solution is preferably obtained by adding the compounds to (3) solvent and then raising the temperature.

(3) Solvent is preferably a solvent that can dissolve the compound containing component B and component X, and the compound containing component A, which are raw materials.

The "high temperature" only needs to be a solvent having a temperature at which each of the raw materials is dissolved. For example, the temperature of the high-temperature (3) solvent is preferably 60 to 600° C., and more preferably 80 to 400° C.

When a solution is obtained by adding the compounds to (3) solvent and then raising the temperature, a holding temperature after the temperature rise is, for example, preferably 80 to 150° C., and more preferably 120 to 140° C.

When a solution is obtained by adding the compounds to (3) solvent and then raising the temperature, a temperature rising rate is preferably 0.1° C./min or more and less than 4° C./min. When the temperature rising rate is within the above range, the unit cell volume of the perovskite compound can be easily controlled within a predetermined range.

The perovskite compound of the present embodiment can be obtained by adjusting the temperature rising rate of the solution during the temperature rise to, for example, 0.1° C./min or more and less than 4° C./min and controlling a micelle size in the reaction solution.

Subsequently, the resulting solution is cooled.

A cooling temperature is preferably −20 to 50° C., and more preferably −10 to 30° C.

A cooling rate is preferably 0.1 to 1500° C./min, and more preferably 10 to 150° C./min.

By cooling the high-temperature solution, the perovskite compound can be precipitated due to a difference in solubility caused by a difference in temperature of the solution. As a result, a dispersion containing the perovskite compound is obtained.

By performing solid-liquid separation on the obtained dispersion containing the perovskite compound, the perovskite compound can be collected. Examples of the solid-liquid separation method include filtration and concentration by evaporation of a solvent. By performing solid-liquid separation, only the perovskite compound can be collected.

Note that the above-described manufacturing method preferably includes a step of adding the above-described (6) surface modifier because the particles of the obtained perovskite compound are easily dispersed stably in the dispersion.

The step of adding (6) surface modifier is preferably performed before the cooling step. Specifically, (6) surface modifier may be added to (3) solvent, or may be added to a solution in which the compound containing component B and component X, and the compound containing component A are dissolved.

The above-described manufacturing method preferably includes a step of removing coarse particles by a method such as centrifugation or filtration after the cooling step. The size of each of the coarse particles to be removed by the removing step is preferably more than 10 μm, more preferably more than 1 μm, and still more preferably more than 500 nm.

(Second Manufacturing Method)

Examples of the method for manufacturing the perovskite compound further include a manufacturing method including a step of obtaining a first solution containing component A and component B, which constitute the perovskite compound, a step of obtaining a second solution containing component X, which constitutes the perovskite compound, a step of mixing the first solution with the second solution to obtain a mixed solution, and a step of cooling the obtained mixed solution.

Hereinafter, the second manufacturing method will be specifically described.

First, the compound containing component A and the compound containing component B are dissolved in the above-described high-temperature (3) solvent to obtain the first solution.

In this step, the compounds may be added to the high-temperature (3) solvent and dissolved to obtain the first solution.

In addition, in this step, the compounds may be added to (3) solvent, and then the temperature may be raised to obtain the first solution. In the second manufacturing method, the first solution is preferably obtained by adding the compounds to (3) solvent and then raising the temperature.

(3) Solvent is preferably a solvent that can dissolve the compound containing component A and the compound containing component B.

The "high temperature" only needs to be a temperature at which the compound containing component A and the compound containing component B are dissolved. For example, the temperature of the high-temperature (3) solvent is preferably 60 to 600° C., and more preferably 80 to 400° C.

When the first solution is obtained by adding the compounds to (3) solvent and then raising the temperature, a holding temperature after the temperature rise is, for example, preferably 80 to 150° C., and more preferably 120 to 140° C.

When the first solution is obtained by adding the compounds to (3) solvent and then raising the temperature, a temperature rising rate is preferably 0.1° C./min or more and less than 4° C./min. When the temperature rising rate is within the above range, the unit cell volume of the perovskite compound can be easily controlled within a predetermined range.

The perovskite compound of the present embodiment can be obtained by adjusting the temperature rising rate of the solution during the temperature rise to, for example, 0.1° C./min or more and less than 4° C./min and controlling a micelle size in the reaction solution.

The compound containing component X is dissolved in the above-described (3) solvent to obtain the second solution. The compound containing component X and the compound containing component B may be dissolved in (3) solvent to obtain the second solution.

Examples of (3) solvent include a solvent that can dissolve the compound containing component X.

Subsequently, the obtained first solution and second solution are mixed to obtain a mixed solution. When the first solution is mixed with the second solution, it is preferable to dropwise add one of the solutions to the other. In addition, the first solution is preferably mixed with the second solution while being stirred.

Subsequently, the obtained mixed solution is cooled.

A cooling temperature is preferably −20 to 50° C., and more preferably −10 to 30° C.

A cooling rate is preferably 0.1 to 1500° C./min, and more preferably 10 to 150° C./min.

By cooling the mixed solution, the perovskite compound can be precipitated due to a difference in solubility caused by a difference in temperature of the mixed solution. As a result, a dispersion containing the perovskite compound is obtained.

By performing solid-liquid separation on the obtained dispersion containing the perovskite compound, the perovskite compound can be collected. Examples of the solid-liquid separation method include the method illustrated for the first manufacturing method.

Note that the above-described manufacturing method preferably includes a step of adding the above-described (6) surface modifier because the particles of the obtained perovskite compound are easily dispersed stably in the dispersion.

The step of adding (6) surface modifier is preferably performed before the cooling step. Specifically, (6) surface modifier may be added to any of (3) solvent, the first solution, the second solution, and the mixed solution.

The above-described manufacturing method preferably includes the step of removing coarse particles by a method such as centrifugation or filtration, described for the first manufacturing method, after the cooling step.

<Composition 1 Manufacturing Method 1>

Hereinafter, in order to make it easier to understand the properties of an obtained composition, a composition obtained by composition 1 manufacturing method 1 will be referred to as "composition 1-1". Composition 1-1 is a liquid composition.

Composition 1-1 of the present embodiment can be manufactured by further mixing (1) perovskite compound and (2) surface protecting agent with either one or both of (3) solvent and (4) polymerizable compound.

When (1) perovskite compound and (2) surface protecting agent are mixed with either one or both of (3) solvent and (4) polymerizable compound, mixing is preferably performed with stirring.

When (1) perovskite compound and (2) surface protecting agent are mixed with (4) polymerizable compound, the temperature during mixing is not particularly limited. The temperature during mixing is preferably within a range of 0° C. to 100° C., and more preferably within a range of 10° C. to 80° C. because (1) perovskite compound and (2) surface protecting agent are easily mixed uniformly.

(Method for Manufacturing Composition 1-1 Containing (3) Solvent)

A method for manufacturing a composition containing (1) perovskite compound, (2) surface protecting agent, and (3) solvent may be, for example, the following manufacturing method (a1) or (a2).

Manufacturing method (a1): a method for manufacturing the composition, the method including a step of mixing (1) perovskite compound with (3) solvent, and a step of mixing the obtained mixture with (2) surface protecting agent.

Manufacturing method (a2): a method for manufacturing the composition, the method including a step of mixing (1) perovskite compound with (2) surface protecting agent, and a step of mixing the obtained mixture with (3) solvent.

(3) Solvent used in manufacturing methods (a1) and (a2) is preferably a solvent that hardly dissolves (1) perovskite compound. When such (3) solvent is used, the mixture obtained by manufacturing method (a1) and the compositions obtained by manufacturing methods (a1) and (a2) are dispersions.

When the composition of the present embodiment contains either one or both of the modified product of the (2-1) silazane and the modified product of the (2-2) silicon compound as (2) surface protecting agent, the method for manufacturing the composition may be the following manufacturing method (a3) or (a4).

Manufacturing method (a3): a method for manufacturing the composition, the method including a step of mixing (1) perovskite compound with (3) solvent, a step of mixing the obtained mixture with either one or both of the (2-1) silazane and the (2-2) silicon compound, and a step of subjecting the obtained mixture to a modification treatment.

Manufacturing method (a4): a method for manufacturing the composition, the method including a step of mixing (1) perovskite compound with either one or both of the (2-1) silazane and the (2-2) silicon compound, a step of mixing the obtained mixture with (3) solvent, and a step of subjecting the obtained mixture to a modification treatment.

In (3) solvent, (5) polymer may be dissolved or dispersed.

In the mixing steps included in the above-described manufacturing methods, it is preferable to perform stirring from a viewpoint of enhancing dispersibility.

In the mixing steps included in the above-described manufacturing methods, the temperature is not particularly limited as long as the temperature make mixing possible. However, the temperature is preferably within a range of 0° C. or higher and 100° C. or lower, and more preferably within a range of 10° C. or higher and 80° C. or lower from a viewpoint of uniform mixing.

The method for manufacturing the composition is preferably manufacturing method (a1) or (a3) from a viewpoint of improving the dispersibility of (1) perovskite compound.

(Method for Performing Modification Treatment)

Examples of the method for performing a modification treatment include known methods such as a method for irradiating the (2-1) silazane and the (2-2) silicon compound with ultraviolet rays and a method for causing the (2-1) silazane and the (2-2) silicon compound to react with water vapor. In the following description, a treatment of causing the (2-1) silazane and the (2-2) silicon compound to react with water vapor may be referred to as "humidification treatment".

The wavelength of an ultraviolet ray used in the ultraviolet ray irradiation method is usually 10 to 400 nm, preferably 10 to 350 nm, and more preferably 100 to 180 nm. Examples of a light source that generates an ultraviolet ray include a metal halide lamp, a high-pressure mercury lamp, a low-pressure mercury lamp, a xenon arc lamp, a carbon arc lamp, an excimer lamp, and UV laser light.

Among the methods, the humidification treatment is preferably performed from a viewpoint of forming a stronger protective region near (1) perovskite compound.

When the humidification treatment is performed, for example, the composition may be allowed to stand for a certain period of time under temperature and humidity conditions described later, or the composition may be stirred for a certain period of time under the same conditions.

The temperature in the humidification treatment only needs to be a temperature at which modification proceeds sufficiently. The temperature in the humidification treatment is, for example, preferably 5 to 150° C., more preferably 10 to 100° C., and still more preferably 15 to 80° C.

The humidity in the humidification treatment only needs to be a humidity at which sufficient moisture is supplied to the (2-1) and the (2-2) in the composition. The humidity in the humidification treatment is, for example, preferably 30% to 100%, more preferably 40% to 95%, and still more preferably 60% to 90%.

The time required for the humidification treatment only needs to be a time during which modification proceeds sufficiently. The time required for the humidification treatment is, for example, preferably 10 minutes or more and one week or less, more preferably one hour or more and five days or less, and still more preferably two hours or more and three days or less.

Stirring is preferably performed from a viewpoint of enhancing the dispersibility of the (2-1) and the (2-2) contained in the composition.

In the humidification treatment, water may be supplied by circulating a gas containing water vapor in a reaction vessel, or water may be supplied from an interface by stirring the mixture in an atmosphere containing water vapor.

When a gas containing water vapor is circulated in a reaction vessel, the flow rate of the gas containing water vapor is preferably 0.01 L/min or more and 100 L/min or less, more preferably 0.1 L/min or more and 10 L/min or less, and still more preferably 0.15 L/min or more and 5 L/min or less because the durability of the obtained composition is improved. Examples of the gas containing water vapor include nitrogen containing a saturated amount of water vapor.

In the method for manufacturing the composition of the present embodiment, (2) surface protecting agent and (3) solvent may be mixed in any step included in the above-described method for manufacturing (1) perovskite compound. For example, the following manufacturing method (a5) or (a6) may be used.

Manufacturing method (a5): a manufacturing method including a step of dissolving a compound containing component B, a compound containing component X, and a compound containing component A, which constitute the perovskite compound, and (2) surface protecting agent in high-temperature (3) solvent to obtain a solution, and a step of cooling the solution.

Manufacturing method (a6): a manufacturing method including a step of dissolving a compound containing component A and a compound containing component B, which constitute the perovskite compound, in (3) solvent to obtain a first solution, a step of dissolving a compound containing component X, which constitutes the perovskite compound, in (3) solvent to obtain a second solution, a step of mixing the first solution with the second solution to obtain a mixed solution, and a step of cooling the obtained mixed solution.

In manufacturing method (a6), (2) surface protecting agent is dissolved in either one or both of the first solution and the second solution.

The conditions of each step included in these manufacturing methods are similar to the conditions of the first manufacturing method and the second manufacturing method in the above-described method for manufacturing (1) perovskite compound.

(Method for Manufacturing Composition 1-1 Containing (4) Polymerizable Compound)

Examples of a method for manufacturing a composition containing (1) perovskite compound, (2) surface protecting agent, and (4) polymerizable compound include the following manufacturing methods (c1) to (c3).

Manufacturing method (c1): a manufacturing method including a step of dispersing (1) perovskite compound in (4) polymerizable compound to obtain a dispersion, and a step of mixing the obtained dispersion with (2) surface protecting agent.

Manufacturing method (c2): a manufacturing method including a step of dispersing (2) surface protecting agent in (4) polymerizable compound to obtain a dispersion, and a step of mixing the obtained dispersion with (1) perovskite compound.

Manufacturing method (c3): a manufacturing method including a step of dispersing a mixture of (1) perovskite compound and (2) surface protecting agent in (4) polymerizable compound.

Among manufacturing methods (c1) to (c3), manufacturing method (c1) is preferable from a viewpoint of enhancing the dispersibility of (1) perovskite compound.

In manufacturing methods (c1) to (c3), in each step of obtaining a dispersion, (4) polymerizable compound may be added dropwise to each material, or each material may be added dropwise to (4) polymerizable compound.

At least one of (1) perovskite compound and (2) surface protecting agent is preferably added dropwise to (4) polymerizable compound because (1) perovskite compound and (2) surface protecting agent are easily uniformly dispersed.

In manufacturing methods (c1) to (c3), in each mixing step, a dispersion may be added dropwise to each material, or each material may be added dropwise to a dispersion.

At least one of (1) perovskite compound and (2) surface protecting agent is preferably added dropwise to a dispersion because (1) perovskite compound and (2) surface protecting agent are easily uniformly dispersed.

At least one of (3) solvent and (5) polymer may be dissolved or dispersed in (4) polymerizable compound.

A solvent for dissolving or dispersing (5) polymer is not particularly limited. The solvent is preferably a solvent that hardly dissolves (1) perovskite compound.

Examples of the solvent in which (5) polymer is dissolved include the above-described (3) solvent.

Among (3) solvents, a halogenated hydrocarbon and a hydrocarbon are more preferable.

The method for manufacturing the composition of the present embodiment may be the following manufacturing method (c4) or (c5).

Manufacturing method (c4): a method for manufacturing the composition, the method including a step of dispersing (1) perovskite compound in (3) solvent to obtain a dispersion, a step of mixing the obtained dispersion with (4) polymerizable compound and (5) polymer to obtain a mixed solution, and a step of mixing the obtained mixed solution with (2) surface protecting agent.

Manufacturing method (c5): a method for manufacturing the composition, the method including a step of dispersing (1) perovskite compound in (3) solvent to obtain a dispersion, a step of mixing the obtained dispersion with either one or both of the (2-1) silazane and the (2-2) silicon compound to obtain a mixed solution, a step of subjecting the obtained mixed solution to a modification treatment to obtain a mixed solution containing either one or both of a modified product of the (2-1) silazane and a modified product of the (2-2) silicon compound, and a step of mixing the obtained mixed solution with (3) solvent.

In composition 1 manufacturing method 1, when (6) surface modifier is used, (6) surface modifier can be added together with (2) surface protecting agent.

<Composition 1 Manufacturing Method 2>

Examples of the method for manufacturing the composition of the present embodiment include a manufacturing method including a step of mixing (1) perovskite compound, (2) surface protecting agent, and (4) polymerizable compound, and a step of polymerizing (4) polymerizable compound.

In a composition obtained by composition 1 manufacturing method 2, the total amount of (1) perovskite compound, (2) surface protecting agent, and (5) polymer is preferably 90% by mass or more of the entire composition.

Examples of the method for manufacturing the composition of the present embodiment also include a manufacturing method including a step of mixing (1) perovskite compound, (2) surface protecting agent, and (5) polymer dissolved in (3) solvent, and a step of removing (3) solvent.

For the mixing steps included in the above-described manufacturing methods, a mixing method similar to the method described in the above-described composition 1 manufacturing method 1 can be used.

Examples of the composition manufacturing method include the following manufacturing methods (d1) and (d2).

Manufacturing method (d1): a manufacturing method including a step of dispersing (1) perovskite compound and (2) surface protecting agent in (4) polymerizable compound, and a step of polymerizing (4) polymerizable compound.

In the dispersing step, the order of adding (1) perovskite compound and (2) surface protecting agent to (5) polymerizable compound is not limited. (1) Perovskite compound may be added first, or (2) surface protecting agent may be added first. Alternatively, (1) perovskite compound and (2) surface protecting agent may be added simultaneously.

Manufacturing method (d2): a manufacturing method including a step of dispersing (1) perovskite compound and (2) surface protecting agent in (3) solvent in which (5) polymer is dissolved, and a step of removing the solvent.

In the dispersing step, the order of adding (1) perovskite compound and (2) surface protecting agent to (5) polymer is not limited. (1) Perovskite compound may be added first, or (2) surface protecting agent may be added first. Alternatively, (1) perovskite compound and (2) surface protecting agent may be added simultaneously.

The step of removing (3) solvent included in manufacturing method (d2) may be a step of allowing a solution to stand at room temperature to naturally dry the solution, a step of drying a solution under reduced pressure using a vacuum dryer, or a step of evaporating (3) solvent by heating.

In the step of removing (3) solvent, for example, (3) solvent can be removed by drying a solution at 0° C. or higher and 300° C. or lower for one minute or more and seven days or less.

The step of polymerizing (4) polymerizable compound included in manufacturing method (d1) can be performed by appropriately using a known polymerization reaction such as radical polymerization.

For example, in the case of radical polymerization, by adding a radical polymerization initiator to a mixture of (1) perovskite compound, (2) surface protecting agent, and (4) polymerizable compound to generate radicals, a polymerization reaction can be caused to proceed.

The radical polymerization initiator is not particularly limited, but examples thereof include a photoradical polymerization initiator.

Examples of the photoradical polymerization initiator include bis(2,4,6-trimethylbenzoyl)-phenylphosphine oxide.

In composition 1 manufacturing method 2, when (6) surface modifier is used, (6) surface modifier can be added together with (2) surface protecting agent.

<Composition 1 Manufacturing Method 3>

As the method for manufacturing the composition of the present embodiment, the following manufacturing methods (d3) to (d6) can also be adopted.

Manufacturing method (d3): a manufacturing method including a step of melt-kneading (1) perovskite compound, (2) surface protecting agent, and (5) polymer.

Manufacturing method (d4): a manufacturing method including a step of melt-kneading (1) perovskite compound, either one or both of the (2-1) silazane and the (2-2) silicon compound, and (5) polymer, and a step of subjecting the obtained mixture to a humidification treatment in a state where (5) polymer is melted.

Manufacturing method (d5): a manufacturing method including a step of manufacturing a liquid composition containing (1) perovskite compound and (2) surface protecting agent, a step of taking out a solid content from the obtained liquid composition, and a step of melt-kneading the obtained solid content and (5) polymer.

Manufacturing method (d6): a manufacturing method including a step of manufacturing a liquid composition not containing (2) surface protecting agent and containing (1) perovskite compound, a step of taking out a solid content from the obtained liquid composition, and a step of melt-kneading the obtained solid content, (2) surface protecting agent, and (5) polymer.

As a method for melt-kneading (5) polymer in manufacturing methods (d3) to (d6), a method known as a method for kneading a polymer can be adopted. For example, extrusion using a single-screw extruder or a twin-screw extruder can be adopted.

As the step of performing a modification treatment in manufacturing method (d4), the above-described method can be adopted.

As the step of manufacturing a liquid composition in manufacturing methods (d5) and (d6), the above-described manufacturing method (a1) or (a2) can be adopted. In the step of manufacturing a liquid composition in manufacturing method (d6), it is only required not to add (2) surface protecting agent in the above-described manufacturing method (a1) or (a2).

As the step of manufacturing a liquid composition in manufacturing method (d5), the above-described manufacturing method (a3) or (a4) can be adopted.

The step of taking out a solid content in manufacturing methods (d5) and (d6) is performed by removing (3) solvent and (4) polymerizable compound, which constitute the liquid composition, from the liquid composition by, for example, heating, reducing the pressure, blowing air, or a combination thereof.

In composition manufacturing method 3, when (6) surface modifier is used, (6) surface modifier can be added together with (2) surface protecting agent.

<Composition 2 Manufacturing Method>

Composition 2 of the present embodiment can be manufactured in a similar manner to the above-described composition 1 manufacturing methods 1 to 3 except that (2) surface protecting agent is not added and a modification treatment is not performed.

In the above-described composition 1 manufacturing method, when a solution containing a halogen ion is added to a composition that has been subjected to a modification treatment, an exchange reaction between X in (1) perovskite compound and the halogen ion occurs, and a value of maximum emission wavelength of (1) perovskite compound can be adjusted.

After a surface protective layer formed of the (2) surface protecting agent is formed on a surface of (1) perovskite compound, a layer of an inorganic silicon compound having a siloxane bond may be further formed.

Here, the "inorganic silicon compound having a siloxane bond" means a modified product of a compound containing an organic group and a silicon element, in which all of the organic groups are organic groups that are eliminated by a modification treatment (hydrolysis), and a modified product of a compound containing a silicon element that does not have an organic group.

Examples of the inorganic silicon compound having a siloxane bond include a modified product of a disilazane in which all of a plurality of $R^{15}$s is hydrogen atoms in the formula (B1), a modified product of a low molecular weight silazane in which all of a plurality of $R^{15}$s is hydrogen atoms in the formula (B2), a modified product of a high molecular weight silazane in which all of a plurality of $R^{15}$s is hydrogen atoms in the formula (B3), a modified product of a high molecular weight silazane in which all of a plurality of $R^{15}$s is hydrogen atoms in a polysilazane having a structure represented by the formula (B4), and a modified product of sodium silicate ($Na_2SiO_3$)

<Measurement of Content of (1) Perovskite Compound Contained in Composition>

The solid content concentration (% by mass) of (1) perovskite compound contained in the composition of the present embodiment can be calculated by a dry mass method. Details of the dry mass method will be described in Examples.

<Measurement of Quantum Yield and Emission Wavelength>

The quantum yield of (1) perovskite compound of the present invention is measured using an absolute PL quantum yield measuring device (for example, C9920-02 manufactured by Hamamatsu Photonics Co., Ltd.) with excitation light of 450 nm at room temperature in the atmosphere. As the emission wavelength, a wavelength having the highest emission intensity is used.

<Film>

The film according to the present invention contains (1) perovskite compound of the present embodiment.

The film according to the present embodiment contains the above-described composition. For example, the film according to the present embodiment contains (1) perovskite compound and (5) polymer, and the total amount of (1) perovskite compound and (5) polymer is 90% by mass or more of the entire film.

The shape of the film is not particularly limited, and may be any shape such as a sheet shape or a bar shape. Here, the "bar shape" means, for example, a plan-view strip shape extending in one direction. Examples of the plan-view strip shape include a plate shape having different side lengths.

The thickness of the film may be 0.01 μm to 1000 mm, 0.1 μm to 10 mm, or 1 μm to 1 mm.

Here, the thickness of the film refers to a distance between a front surface and a back surface in a thickness direction of the film when a side having the smallest value among the length, the width, and the height of the film is defined as the "thickness direction". Specifically, the thicknesses of the film are measured at any three points of the film using a micrometer, and an average value of the measured values at the three points is taken as the thickness of the film.

The film may be a single-layered film or a multi-layered film. In the case of the multi-layered film, the same type of composition of the embodiment may be used for the layers, or different types of compositions of the embodiment may be used for the layers.

As the film, for example, a film formed on a substrate can be obtained by a method for manufacturing a layered structure described later. The film can be obtained by peeling the film from the substrate.

<Layered Structure>

The layered structure according to the present embodiment has a plurality of layers, and at least one layer is the above-described film.

Among the plurality of layers of the layered structure, examples of a layer other than the above-described film include any layer such as a substrate, a barrier layer, or a light scattering layer.

The shape of the film to be stacked is not particularly limited, and may be any shape such as a sheet shape or a bar shape.

(Substrate)

The substrate is not particularly limited, but may be a film. The substrate is preferably light-transmitting. A layered structure having a light-transmitting substrate is preferable because light emitted by (1) perovskite compound is easily extracted.

As a material for forming the substrate, for example, a known material such as a polymer including polyethylene terephthalate or glass can be used.

For example, the layered structure may include the above-described film on the substrate.

FIG. 1 is a cross-sectional view schematically illustrating the structure of the layered structure of the present embodiment. A first layered structure 1a includes a film 10 of the present embodiment between a first substrate 20 and a second substrate 21. The film 10 is sealed with a sealing layer 22.

An aspect of the present invention is a layered structure 1a including the first substrate 20, the second substrate 21, the film 10 according to the present embodiment located between the first substrate 20 and the second substrate 21, and the sealing layer 22, characterized in that the sealing layer 22 is disposed on a surface of the film 10 not in contact with the first substrate 20 or the second substrate 21.

(Barrier layer)

A layer that may be included in the layered structure according to the present embodiment is not particularly limited, but examples thereof include a barrier layer. A barrier layer may be included from a viewpoint of protecting the above-described composition from water vapor of the outside air and the air in the atmosphere.

The barrier layer is not particularly limited, but a transparent layer is preferable from a viewpoint of extracting emitted light. As the barrier layer, for example, a known barrier layer such as a polymer including polyethylene terephthalate or a glass film can be used.

(Light Scattering Layer)

A layer that may be included in the layered structure according to the present embodiment is not particularly limited, but examples thereof include a light scattering layer. The light scattering layer may be included from a viewpoint of effectively utilizing incident light.

The light scattering layer is not particularly limited, but a transparent layer is preferable from a viewpoint of extracting emitted light. As the light scattering layer, a known light scattering layer such as light scattering particles including silica particles or an amplified diffusion film can be used.

<Light-Emitting Device>

The light-emitting device according to the present invention can be obtained by combining the compound, the composition, or the layered structure according to the embodiment of the present invention with a light source. The light-emitting device irradiates the composition or the layered structure disposed in a subsequent stage with light emitted from the light source to cause the composition or the layered structure to emit light, and extracts light. Among the plurality of layers included in the layered structure in the light-emitting device, examples of a layer other than the above-described film, substrate, barrier layer, and light scattering layer include any layer such as a light reflecting member, a brightness enhancing portion, a prism sheet, a light guide plate, or a medium material layer between elements.

One aspect of the present invention is a light-emitting device 2 in which a prism sheet 50, a light guide plate 60, the first layered structure 1a, and a light source 30 are stacked in this order.

(Light Source)

The light source constituting the light-emitting device according to the present invention is not particularly limited, but a light source having an emission wavelength of 600 nm or less is preferable from a viewpoint of causing (1) perovskite compound in the above-described compound, composition, or layered structure to emit light. As the light source, for example, a known light source such as a light-emitting diode (LED) including a blue light-emitting diode, a laser, or EL can be used.

(Light Reflecting Member)

A layer that may be included in the layered structure constituting the light-emitting device according to the present invention is not particularly limited, but examples thereof include a light reflecting member. The light reflecting member may be included from a viewpoint of irradiating the composition or the layered structure with light of the light source. The light reflecting member is not particularly limited, but may be a reflective film.

As the reflective film, for example, a known reflective film such as a reflecting mirror, a film of reflective particles, a reflective metal film, or a reflector can be used.

(Brightness Enhancing Portion)

A layer that may be included in the layered structure constituting the light-emitting device according to the present invention is not particularly limited, but examples thereof include a brightness enhancing portion. The brightness enhancing portion may be included from a viewpoint of reflecting a part of light back in a direction in which the light is transmitted.

(Prism Sheet)

A layer that may be included in the layered structure constituting the light-emitting device according to the present invention is not particularly limited, but examples thereof include a prism sheet. The prism sheet typically includes a base material portion and a prism portion. Note that the base material portion may be omitted depending on an adjacent member. The prism sheet can be stuck on an adjacent member via any suitable adhesive layer (for example, an adhesive layer or a pressure-sensitive adhesive layer). The prism sheet has a plurality of unit prisms protruding from a side (back side) opposite to a viewing side arranged in parallel. By arranging the protruding portions of the prism sheet toward the back side, light that passes through the prism sheet can be easily collected. In addition, when the protruding portions of the prism sheet are arranged toward the back side, the amount of light to be reflected without being incident on the prism sheet is smaller than that in a case where the protruding portions are arranged toward the viewing side, and a display having high brightness can be obtained.

(Light Guide Plate)

A layer that may be included in the layered structure constituting the light-emitting device according to the present invention is not particularly limited, but examples thereof include a light guide plate. As the light guide plate, for example, any suitable light guide plate such as a light guide plate having a lens pattern formed on the back side, or having a prism shape or the like on the back side and/or the viewing side such that light from a lateral direction can be deflected in the thickness direction can be used.

(Medium Material Layer Between Elements)

A layer that may be included in the layered structure constituting the light-emitting device according to the present invention is not particularly limited, but examples thereof include a layer (medium material layer between elements) containing one or more medium materials on an optical path between adjacent elements (layers).

The one or more media contained in the medium material layer between elements is not particularly limited, but examples thereof include vacuum, air, gas, an optical material, an adhesive, an optical adhesive, glass, a polymer, solid, liquid, gel, a curing material, an optical coupling material, a refractive index-matching or refractive index-mismatching material, a refractive index gradient material, a cladding or anti-cladding material, a spacer, silica gel, a brightness enhancing material, a scattering or diffusing material, a reflective or anti-reflective material, a wavelength selecting material, a wavelength selecting anti-reflective material, a color filter, and a suitable medium known in the above field of the technology.

Specific examples of the light-emitting device according to the present invention include a device including a wavelength conversion material for an EL display or a liquid crystal display.

Specific examples of the light-emitting device according to the present invention include:

(E1) a backlight that converts blue light into green light or red light, in which the composition of the present invention is put in a glass tube or the like, and the glass tube or the like is sealed and disposed between a blue light-emitting diode as a light source and a light guide plate along an end surface (side surface) of the light guide plate (on-edge type backlight), (E2) a backlight that converts blue light emitted from a blue light-emitting diode disposed on an end surface (side surface) of a light guide plate to a sheet through the light guide plate into green light or red light, in which the composition of the present invention is formed into the sheet, the sheet is sandwiched between two barrier films and sealed to obtain a film, and the film is disposed on the light guide plate (surface mount type backlight);

(E3) a backlight that converts emitted blue light into green light or red light, in which the composition of the present invention is dispersed in a resin or the like and disposed near a light-emitting portion of a blue light-emitting diode (on-chip type backlight); and (E4) a backlight that converts blue light emitted from a light source into green light or red light, in which the composition of the present invention is dispersed in a resist and disposed on a color filter.

Specific examples of the light-emitting device according to the present invention also include a lighting that converts blue light into green light or red light to emit white light, in which the composition of the embodiment of the present invention is molded and disposed in a subsequent stage of a blue light-emitting diode as a light source.

<Display>

Figure 2:
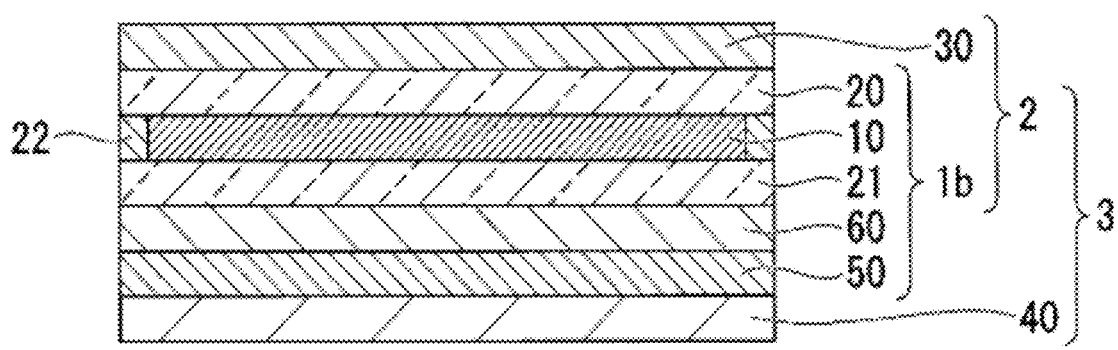
FIG. 2 is a cross-sectional view illustrating an embodiment of a display according to the present invention.

As illustrated in FIG. 2, a display 3 of the present embodiment includes a liquid crystal panel 40 and the above-described light-emitting device 2 in this order from the viewing side. The light-emitting device 2 includes a second layered structure 1b and the light source 30. The second layered structure 1b is obtained by adding the prism sheet 50 and the light guide plate 60 to the above-described first layered structure 1a. The display may further include any suitable other components.

One aspect of the present invention is the liquid crystal display 3 in which the liquid crystal panel 40, the prism sheet 50, the light guide plate 60, the first layered structure 1a, and the light source 30 are stacked in this order.

(Liquid Crystal Panel)

The liquid crystal panel typically includes a liquid crystal cell, a viewing side polarizing plate disposed on the viewing side of the liquid crystal cell, and a back side polarizing plate disposed on the back side of the liquid crystal cell. The viewing side polarizing plate and the back side polarizing plate can be disposed such that absorption axes thereof are substantially orthogonal or parallel to each other.

(Liquid Crystal Cell)

The liquid crystal cell includes a pair of substrates and a liquid crystal layer as a display medium sandwiched between the substrates. In a general structure, one substrate includes a color filter and a black matrix, and the other substrate includes a switching element that controls electro-optical characteristics of a liquid crystal, a scanning line that supplies a gate signal to the switching element, a signal line that supplies a source signal to the switching element, a pixel electrode, and a counter electrode. A distance between the substrates (cell gap) can be controlled by a spacer or the like. For example, an alignment film containing polyimide can be disposed on a side of each of the substrates in contact with the liquid crystal layer.

(Polarizing Plate)

The polarizing plate typically includes a polarizer and protective layers disposed on both sides of the polarizer. The polarizer is typically an absorption-type polarizer.

As the polarizer, any suitable polarizer is used. Examples thereof include a polarizer obtained by making a dichroic substance such as iodine or a dichroic dye adsorbed on a hydrophilic polymer film such as a polyvinyl alcohol-based film, a partially formalized polyvinyl alcohol-based film, or an ethylene-vinyl acetate copolymer-based partially saponified film, and uniaxially stretching the resulting film, and a polyene-based oriented film such as a polyvinyl alcohol dehydrated product or a polyvinyl chloride dehydrochlorinated product. Among these polarizers, a polarizer obtained by making a dichroic substance such as iodine adsorbed on a polyvinyl alcohol-based film, and uniaxially stretching the resulting film is particularly preferable because of having a high polarization dichroic ratio.

Examples of an application of the compound or composition of the present embodiment include a wavelength conversion material for a light-emitting diode (LED).

<LED>

The compound or composition of the present embodiment can be used, for example, as a material of a light emitting layer of an LED.

Examples of the LED containing the compound or composition of the present embodiment include an LED having a structure in which the compound or composition of the present embodiment and conductive particles such as ZnS are mixed and stacked in a film form, an n-type transport layer is stacked on one side, and a p-type transport layer is stacked on the other side, in which holes in the p-type semiconductor and electrons in the n-type semiconductor cancel out charges in particles of (1) perovskite compound contained in the composition in a bonding surface when a current flows, and the LED thereby emits light.

<Solar cell>

The compound or composition of the present embodiment can be used as an electron transporting material contained in an active layer of a solar cell.

The structure of the solar cell is not particularly limited, but examples of the solar cell include a solar cell including a fluorine-doped tin oxide (FTO) substrate, a titanium oxide dense layer, a porous aluminum oxide layer, an active layer containing the compound or composition of the present embodiment, a hole transport layer such as 2,2',7,7'-tetrakis (N,N'-di-p-methoxyphenylamine)-9,9'-spirobifluorene (Spiro-MeOTAD), and a silver (Ag) electrode in this order.

The titanium oxide dense layer has a function of electron transport, an effect of suppressing the roughness of FTO, and a function of suppressing reverse electron transfer.

The porous aluminum oxide layer has a function of improving light absorption efficiency.

The compound or composition of the present embodiment contained in the active layer has functions of charge separation and electron transport.

<Method for Manufacturing Film>

Examples of a method for manufacturing the film include the following manufacturing methods (e1) to (e3).

Manufacturing method (e1): a method for manufacturing the film, the method including a step of coating a substrate with a liquid composition to obtain a coating film, and a step of removing (3) solvent from the coating film.

Manufacturing method (e2): a method for manufacturing the film, the method including a step of coating a substrate with a liquid composition containing (4) polymerizable compound to obtain a coating film, and a step of polymerizing (4) polymerizable compound contained in the obtained coating film.

Manufacturing method (e3): a method for manufacturing the film, the method including molding a composition obtained by any one of the above-described manufacturing methods (d1) and (d2).

<<Method for Manufacturing Layered Structure>>

Examples of a method for manufacturing the layered structure include the following manufacturing methods (f1) to (f3).

Manufacturing method (f1): a method for manufacturing the layered structure, the method including a step of manufacturing a liquid composition, a step of coating a substrate with the obtained liquid composition, and a step of removing (3) solvent from the obtained coating film.

Manufacturing method (f2): a method for manufacturing the layered structure, the method including a step of bonding a film to a substrate.

Manufacturing method (f3): a manufacturing method including a step of manufacturing a liquid composition containing (4) polymerizable compound, a step of coating a substrate with the obtained liquid composition, and a step of polymerizing (4) polymerizable compound contained in the obtained coating film.

As the step of manufacturing a liquid composition in each of the manufacturing methods (f1) and (f3), the above-described manufacturing methods (c1) to (c4) can be adopted.

The step of coating a substrate with a liquid composition in each of the manufacturing methods (f1) and (f3) is not particularly limited, but a known applying or coating method such as a gravure applying method, a bar applying method, a printing method, a spray method, a spin coating method, a dip method, or a die coating method can be used.

The step of removing (3) solvent in manufacturing method (f1) can be similar to the step of removing (3) solvent included in the above-described manufacturing method (d2).

The step of polymerizing (4) polymerizable compound in manufacturing method (f3) can be similar to the step of polymerizing (4) polymerizable compound included in the above-described manufacturing method (d1).

Any adhesive can be used in the step of bonding a film to a substrate in the manufacturing method (f2).

The adhesive is not particularly limited as long as the adhesive does not dissolve (1) perovskite compound, and a known adhesive can be used.

The layered structure manufacturing method may further include a step of bonding any film to the obtained layered structure.

Examples of any film to be bonded include a reflective film and a diffusion film.

Any adhesive can be used in the step of bonding a film.

The above-described adhesive is not particularly limited as long as the adhesive does not dissolve (1) perovskite compound, and a known adhesive can be used.

<Method for Manufacturing Light-Emitting Device>

Examples of a method for manufacturing the light-emitting device include a manufacturing method including a step of disposing the above-described light source and the above-described compound, composition, or layered structure on an optical path in a subsequent stage with respect to the light source.

Note that the technical scope of the present invention is not limited to the above-described embodiment, and various modifications can be made without departing from the gist of the present invention.

<Sensor>

The compound or composition of the present embodiment can be used as a photoelectric conversion element (photodetector) material included in an image detection unit (image sensor) for a solid-state imaging device such as an X-ray imaging device or a CMOS image sensor, a detection unit that detects predetermined features of a part of a living body, such as a fingerprint detection unit, a face detection unit, a vein detection unit, or an iris detection unit, or a detection unit of an optical biosensor such as a pulse oximeter.

EXAMPLES

Hereinafter, the present invention will be described in more detail based on Examples and Comparative Examples, but the present invention is not limited to the following Examples.

(Measurement of Solid Content Concentration of (1) Perovskite Compound)

The solid content concentration of the perovskite compound in the composition obtained in Example 6 was determined by drying a dispersion containing the perovskite compound and a solvent obtained by redispersion at 105° C. for three hours, then measuring the mass of the residue, and performing calculation by applying the mass to the following formula 2.

Solid content concentration (% by mass)=mass after drying/mass before drying×100    Formula 2

(Measurement of Quantum Yield and Emission Wavelength)

The quantum yield of each of the compositions obtained in Examples 1 to 6 and Comparative Example 1 was measured using an absolute PL quantum yield measuring device (C9920-02 manufactured by Hamamatsu Photonics Co., Ltd.) with excitation light of 450 nm at room temperature in the atmosphere.

The compound of the present embodiment preferably has a quantum yield of 50% or more. The higher the quantum yield is, the better the compound is. As the emission wavelength, a wavelength having the highest emission intensity in the emission spectrum when the quantum yield was measured by the above-described method was used. The emission wavelength is preferably 530 nm or more and less than 540 nm.

(Measurement of Unit Cell Volume)

The unit cell volume of each of the compounds obtained in Examples 1 to 6 and Comparative Example 1 was measured by X-ray structural diffraction (XRD, CuKα ray, X'pert PRO MPD, manufactured by Spectris Corporation).

The dispersion containing each of the compounds of Examples 1 to 6 and Comparative Example 1 was cast on a non-reflective plate, and naturally dried. Thereafter, measurement was performed, and an interplanar spacing of a unit cell was calculated using Bragg's formula from the X-ray diffraction pattern, a cube of the interplanar spacing of the unit cell was determined, and the unit cell volume was determined by the following formula 1.

Unit cell volume (nm$^3$)=($\lambda$/(2·sin θ))$^3$    Formula 1

In the formula 1, $\lambda$ is 0.15418 nm. As θ, a value of 2θ corresponding to a peak having the strongest intensity among peaks corresponding to d(100) of (1) perovskite compound was adopted.

Example 1

(Manufacture of (1) Perovskite Compound)

25 mL of oleylamine and 200 mL of ethanol were mixed. Thereafter, 17.12 mL of a hydrobromic acid solution (48%) was added thereto while being stirred and cooled with ice. Thereafter, the resulting mixture was dried under reduced pressure to obtain a precipitate. The precipitate was washed with diethyl ether and then dried under reduced pressure to obtain oleylammonium bromide.

200 mL of toluene was mixed with 21 g of oleyl ammonium bromide to prepare a solution containing oleyl ammonium bromide.

0.38 g of lead acetate trihydrate, 0.39 g of formamidine acetate, 40 mL of 1-octadecene solvent, and 10 mL of oleic acid were mixed. The resulting mixture was heated to 130° C. at 0.5° C./min while the mixture was stirred and nitrogen was caused to pass through the mixture. Thereafter, 13.35 mL of the above-described solution containing oleylammonium bromide was added thereto. After the addition, the temperature of the solution was lowered to room temperature to obtain dispersion 1 containing (1) perovskite compound.

When the emission characteristics of a solution obtained by mixing 3.95 mL of toluene with 50 µL of dispersion 1 were evaluated, the quantum yield was 77.9%.

The obtained dispersion 1 containing (1) perovskite compound was cast on a non-reflective plate, and then XRD measurement was performed. As a result, the XRD spectrum had a peak derived from (hkl)=(001) at a position of 2θ=14 to 15°. From the measurement result, it was confirmed that the collected dispersion 1 contained a compound having a three-dimensional perovskite type crystal structure.

The unit cell volume calculated from the result of XRD measurement was 0.2150 nm$^3$.

Example 2

Dispersion 2 was obtained in a similar manner to the Example 1 except that the temperature rising rate to 130° C. in the step of manufacturing a perovskite compound was changed to 2° C./min.

When the emission characteristics were evaluated by a method similar to Example 1 using dispersion 2, the quantum yield was 80.4%.

When XRD measurement was performed using dispersion 2, it was confirmed that dispersion 2 contained a compound having a three-dimensional perovskite type crystal structure.

The unit cell volume calculated from the result of XRD measurement was 0.2135 nm$^3$.

Example 3

Dispersion 3 was obtained in a similar manner to the Example 1 except that the temperature rising rate to 130° C. in the step of manufacturing a perovskite compound was changed to 1° C./min and then the temperature was held for 30 minutes.

When the emission characteristics were evaluated by a method similar to Example 1 using dispersion 3, the quantum yield was 82.4%.

When XRD measurement was performed using dispersion 3, it was confirmed that dispersion 3 contained a compound having a three-dimensional perovskite type crystal structure.

The unit cell volume calculated from the result of XRD measurement was 0.2128 nm$^3$.

Example 4

Dispersion 4 was obtained in a similar manner to the Example 1 except that the temperature rising rate to 130° C. in the step of manufacturing a perovskite compound was changed to 1.3° C./min.

When the emission characteristics were evaluated by a method similar to Example 1 using dispersion 4, the quantum yield was 75.1%.

When XRD measurement was performed using dispersion 4, it was confirmed that dispersion 4 contained a compound having a three-dimensional perovskite type crystal structure.

The unit cell volume calculated from the result of XRD measurement was 0.2077 nm$^3$.

Example 5

25 mL of oleylamine and 200 mL of ethanol were mixed. Thereafter, 17.12 mL of a hydrobromic acid solution (48%) was added thereto while being stirred and cooled with ice. Thereafter, the resulting mixture was dried under reduced pressure to obtain a precipitate. The precipitate was washed with diethyl ether and then dried under reduced pressure to obtain oleylammonium bromide.

200 mL of toluene was mixed with 21 g of oleyl ammonium bromide to prepare a solution containing oleyl ammonium bromide.

1.52 g of lead acetate trihydrate, 1.56 g of formamidine acetate, 160 mL of 1-octadecene solvent, and 40 mL of oleic acid were mixed. The resulting mixture was heated to 130° C. at 1° C./min while the mixture was stirred. Thereafter, 53.4 mL of the above-described solution containing oleylammonium bromide was added thereto. After the addition, the temperature of the solution was lowered to room temperature to obtain dispersion 5 containing (1) perovskite compound.

When the emission characteristics were evaluated by a method similar to Example 1 using dispersion 5, the quantum yield was 73.1%, and the emission wavelength was 540.0 nm.

When XRD measurement was performed using dispersion 5, it was confirmed that dispersion 5 contained a compound having a three-dimensional perovskite type crystal structure.

The unit cell volume calculated from the result of XRD measurement was 0.2063 nm$^3$.

Example 6

Dispersion 6 was obtained in a similar manner to the Example 5. The unit cell volume calculated by the above-described method was 0.2063 nm$^3$.

A solution obtained by mixing 100 mL of toluene and 50 mL of acetonitrile with 200 mL of the above dispersion 5 was subjected to solid-liquid separation by filtration. Thereafter, the solid content on the filtration was washed by causing a mixed solution of 100 mL of toluene and 50 mL of acetonitrile to pass through the solid content twice to perform filtration. As a result, a perovskite compound was obtained.

The above-described perovskite compound was mixed with toluene to prepare 200 mL of dispersion 6 such that the solid content concentration was 0.23% by mass. To the obtained dispersion 6, organopolysilazane (1500 Slow Cure, Durazane, manufactured by Merck Performance Materials Co., Ltd.) was added such that the amount of the organopolysilazane was 1.9 parts by mass with respect to 1 part by mass of the perovskite compound in dispersion 6. Thereafter, the resulting mixture was subjected to a modification treatment with water vapor for four hours to obtain a composition.

As modification treatment conditions at this time, the flow rate of the water vapor was 0.2 L/min (supplied with $N_2$ gas, the amount of saturated water vapor at 30° C.), and the heating temperature was 80° C.

When the emission characteristics were evaluated by the above-described method, the quantum yield was 97.4%. The emission wavelength was 535.9 nm.

Comparative Example 1

Dispersion 7 was obtained in a similar manner to the Example 1 except that the temperature rising rate in the step of manufacturing a perovskite compound was changed to 4° C./min.

When the emission characteristics were evaluated by a method similar to Example 1 using dispersion 7, the quantum yield was 48.4%.

When XRD measurement was performed using dispersion 7, it was confirmed that dispersion 7 contained a compound having a three-dimensional perovskite type crystal structure.

The unit cell volume calculated from the result of XRD measurement was 0.2164 $nm^3$.

The results of Example 1 to 6 and Comparative Example 1 are illustrated in Table 1.

TABLE 1

| | Unit cell volume $nm^3$ | Quantum yield % |
|---|---|---|
| Example 1 | 0.2150 | 77.9 |
| Example 2 | 0.2135 | 80.4 |
| Example 3 | 0.2128 | 82.4 |
| Example 4 | 0.2077 | 75.1 |
| Example 5 | 0.2063 | 73.1 |
| Example 6 | 0.2063 | 97.4 |
| Comparative Example 1 | 0.2164 | 48.4 |

From the above results, it was confirmed that each of the compositions according to Examples 1 to 6 to which the present invention was applied had a higher quantum yield than the composition of Comparative Example 1 to which the present invention was not applied. In addition, it was confirmed that the composition according to Example 6 containing a modified product of silazane had a particularly high quantum yield and could shorten the emission wavelength.

Reference Example 1

By putting each of the compounds or compositions according to Examples 1 to 6 in a glass tube or the like, sealing the glass tube or the like, and then disposing the glass tube or the like between a blue light-emitting diode as a light source and a light guide plate, a backlight that can convert blue light of the blue light-emitting diode into green light or red light is manufactured.

Reference Example 2

By forming each of the compounds or compositions according to Examples 1 to 6 into a sheet to obtain a resin composition, sandwiching the resin composition between two barrier films, sealing the films to obtain a film, and disposing the film on a light guide plate, a backlight that can convert blue light emitted from a blue light-emitting diode disposed on an end surface (side surface) of the light guide plate to the sheet through the light guide plate into green light or red light is manufactured.

Reference Example 3

By disposing each of the compounds or compositions according to Examples 1 to 6 near a light-emitting portion of a blue light-emitting diode, a backlight that can convert blue light emitted into green light or red light is manufactured Reference Example 4

By mixing each of the compounds or compositions according to Examples 1 to 6 with a resist and then removing a solvent, a wavelength conversion material can be obtained. By disposing the obtained wavelength conversion material between a blue light-emitting diode as a light source and a light guide plate or in a subsequent stage of OLED as a light source, a backlight that can convert blue light of the light source into green light or red light is manufactured.

Reference Example 5

By mixing each of the compounds or compositions according to Examples 1 to 6 with conductive particles such as ZnS to form a film, stacking an n-type transport layer on one side, and stacking a p-type transport layer on the other side, an LED is obtained. Holes in the p-type semiconductor and electrons in the n-type semiconductor cancel out charges in a perovskite compound in a bonding surface when a current flows, and the LED can thereby emit light.

Reference Example 6

By stacking a titanium oxide dense layer on a surface of a fluorine-doped tin oxide (FTO) substrate, stacking a porous aluminum oxide layer on the titanium oxide dense layer, stacking each of the compounds or compositions according to Examples 1 to 6 on the porous aluminum oxide layer, removing a solvent, then stacking a hole transport layer such as 2,2',7,7'-tetrakis-(N,N'-di-p-methoxyphenylamine)-9,9'-spirobifluorene (Spiro-OMeTAD) on the composition, and stacking a silver (Ag) layer on the hole transport layer, a solar cell is manufactured.

Reference Example 7

By removing a solvent from each of the compounds or compositions according to Examples 1 to 6 and molding the composition to obtain the composition of the present embodiment, and disposing the composition in a subsequent stage of a blue light-emitting diode, a laser diode lighting that converts blue light emitted from the blue light-emitting diode onto the composition into green light or red light to emit white light is manufactured.

Reference Example 8

By removing a solvent from each of the compounds or compositions according to Examples 1 to 6 and molding the composition, the composition of the present embodiment can be obtained. By using the obtained composition as a part of a photoelectric conversion layer, a photoelectric conversion element (photodetector) material included in a detection unit that detects light is manufactured. The photoelectric conversion element material is used as an image detection unit (image sensor) for a solid-state imaging device such as an X-ray imaging device or a CMOS image sensor, a detection unit that detects predetermined features of a part of a living body, such as a fingerprint detection unit, a face detection unit, a vein detection unit, or an iris detection unit, or an optical biosensor such as a pulse oximeter.

INDUSTRIAL APPLICABILITY

The present invention can provide a compound having a perovskite type crystal structure with a high quantum yield, a composition containing the compound, a film containing the composition, a layered structure including the film, and a light-emitting device and a display each including the layered structure.

Therefore, the compound having a perovskite type crystal structure of the present invention, a composition containing the compound, a film containing the composition, a layered structure including the film, and a light-emitting device and a display each including the layered structure can be suitably used for light emission.

DESCRIPTION OF REFERENCE SIGNS

1a First layered structure
1b Second layered structure
10 Film
20 First substrate
21 Second substrate
22 Sealing layer
2 Light-emitting device
3 Display
30 Light source
40 Liquid crystal panel
50 Prism sheet
60 Light guide plate

The invention claimed is:

1. A composition comprising
(i) a compound having a perovskite type crystal structure comprising
a metal ion,
a monovalent cation located at each apex of a hexahedron centered on the metal ion in the perovskite type crystal structure, and
a halide ion located at each apex of an octahedron centered on the metal ion in the perovskite type crystal structure,
wherein the perovskite type crystal structure has a unit cell volume of 0.2000 nm³ or more and 0.2150 nm³ or less,
an ionic radius of the metal ion is 0.7 Å or more and 1.4 Å or less, and
an ionic radius of the halide ion is 0.5 Å or more and 2.5 Å or less; and
(ii) at least one compound selected from the group consisting of the following (2-1), a modified product of the following (2-1), the following (2-2), and a modified product of the following (2-2):
(2-1) silazane, and
(2-2) silicon compound having at least one group selected from the group consisting of an amino group, an alkoxy group, and an alkylthio group.

2. The composition according to claim 1, wherein the monovalent cation is at least one cation selected from the group consisting of an organic ammonium ion and an amidinium ion.

3. The composition according to claim 1, wherein the metal ion is at least one metal ion selected from the group consisting of a lead ion, a tin ion, an antimony ion, and a bismuth ion.

4. The composition according to claim 1, wherein the halide ion is a bromide ion.

5. The composition according to claim 1, further comprising at least one selected from the group consisting of the following (3), the following (4), and the following (5),
(3) solvent
(4) polymerizable compound
(5) polymer.

6. The composition according to claim 1, wherein the compound comprises silazane.

7. The composition according to claim 1, wherein the compound comprises silicon compound having at least one group selected from the group consisting of an amino group, an alkoxy group, and an alkylthio group.

8. The composition according to claim 1, wherein the metal ion comprises a lead ion.

9. The composition according to claim 1, wherein the metal ion comprises a tin ion.

10. The composition according to claim 1, further comprising polymerizable compound.

11. The composition according to claim 1, further comprising polymer.

12. The composition according to claim 1, wherein the monovalent cation comprises an organic ammonium ion.

13. A film comprising the composition according to claim 1.

14. A layered structure comprising the film according to claim 13.

15. A light-emitting device comprising the layered structure according to claim 14.

16. A display comprising the layered structure according to claim 14.

17. A composition comprising
(i) a compound having perovskite type crystal structure comprising
a metal ion,
a monovalent cation located at each apex of a hexahedron centered on the metal ion in the perovskite type crystal structure, and
a halide ion located at each apex of an octahedron centered on the metal ion in the perovskite type crystal structure,
wherein the perovskite type crystal structure has a unit cell volume of 0.2000 nm³ or more and 0.2150 nm³ or less,
an ionic radius of the metal ion is 0.7 Å or more and 1.4 Å or less; and
(ii) at least one compound selected from the group consisting of the following (2-1), a modified product of the following (2-1), the following (2-2), and a modified product of the following (2-2):
(2-1) silazane, and
(2-2) silicon compound having at least one group selected from the group consisting of an amino group, an alkoxy group, and an alkylthio group.

* * * * *